(12) United States Patent
Chen et al.

(10) Patent No.: US 8,569,265 B2
(45) Date of Patent: Oct. 29, 2013

(54) DEUTERATED ANALOGS OF (4S)-4-ETHYL-4-HYDROXY-11-[2-(TRIMETHYLSILYL)ETHYL]-1H-PYRANO[3',4':6,7] INDOLIZINO [1,2-B]QUINOLINE-3,14(4H, 12H)-DIONE AND METHODS OF USE THEREOF

(75) Inventors: Xinghai Chen, San Antonio, TX (US); Qiuli Huang, San Antonio, TX (US); Harry Kochat, San Antonio, CA (US); Andrey Malakhov, San Antonio, TX (US); Frederick H. Hausheer, Fair Oaks Ranch, TX (US)

(73) Assignee: BioNumerik Pharmaceuticals, Inc., San Antonio, TX (US)

( * ) Notice: Subject to any disclaimer, the term of this patent is extended or adjusted under 35 U.S.C. 154(b) by 253 days.

(21) Appl. No.: 13/068,244

(22) Filed: May 6, 2011

(65) Prior Publication Data

US 2012/0282261 A1    Nov. 8, 2012

(51) Int. Cl.
*A61K 31/695*    (2006.01)
*C07F 7/02*    (2006.01)

(52) U.S. Cl.
USPC .............................................. 514/63; 546/14

(58) Field of Classification Search
USPC ....................................... 514/63, 283; 546/14
See application file for complete search history.

(56) References Cited

U.S. PATENT DOCUMENTS 6,136,978 A * 10/2000 Curran et al. ................... 546/14

* cited by examiner

*Primary Examiner* — Charanjit Aulakh
(74) *Attorney, Agent, or Firm* — Scott A. Whitaker

(57) ABSTRACT

The present invention discloses: (i) two novel deuterated Karenitecin® analogs, pharmaceutically-acceptable salts, and/or derivatives thereof; (ii) methods of synthesis of said novel deuterated Karenitecin® analogs, pharmaceutically-acceptable salts, and/or derivatives thereof; (iii) pharmaceutically-acceptable formulations comprising said novel deuterated Karenitecin® analogs, pharmaceutically-acceptable salts, derivatives thereof; and/or, optionally, one or more additional chemotherapeutic agents; and (iv) methods of administration of said novel deuterated Karenitecin® analogs, pharmaceutically-acceptable salts, derivatives thereof; and/or, optionally, one or more additional chemotherapeutic agents, to subjects in need thereof.

12 Claims, 1 Drawing Sheet

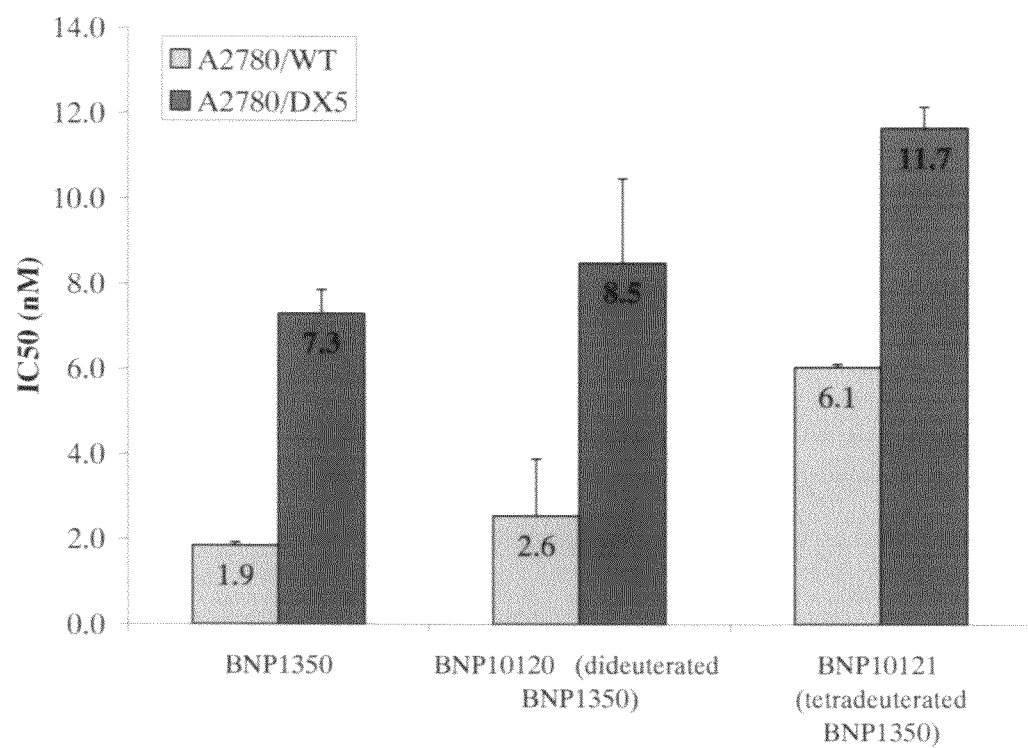

US 8,569,265 B2

DEUTERATED ANALOGS OF (4S)-4-ETHYL-4-HYDROXY-11-[2-(TRIMETHYLSILYL)ETHYL]-1H-PYRANO[3',4':6,7] INDOLIZINO [1,2-B]QUINOLINE-3,14(4H, 12H)-DIONE AND METHODS OF USE THEREOF

FIELD OF THE INVENTION

The present invention relates to novel compounds comprising deuterated analogs of (4S)-4-Ethyl-4-hydroxy-11-[2-(trimethylsilyl)ethyl]-1H-pyrano[3',4':6,7]indolizino[1,2-b]quinoline-3,14(4H,12H)-dione (also known as 7-[2-trimethylsilyl)ethyl]-20(S)-camptothecin; BNP1350; and Karenitecin®), and pharmaceutically-acceptable salts and/or derivatives thereof. The present invention also relates to methods of synthesis and formulations comprising one or more compounds of the present invention and the use of the disclosed compounds and formulations in treating diseases and conditions that are beneficially treated by administering said novel deuterated analogs of (4S)-4-Ethyl-4-hydroxy-11-[2-(trimethylsilyl)ethyl]-1H-pyrano[3',4':6,7]indolizino[1,2-b]quinoline-3,14(4H,12H)-dione, and pharmaceutically-acceptable salts and/or derivatives thereof.

BACKGROUND OF THE INVENTION

Isotopes are atoms which have different masses due to changes in the number of neutrons in their nuclei. One of the most widely used stable isotopes in the pharmaceutical industry is deuterium (D; $^2$H), an isotope of hydrogen with a nucleus comprising one neutron and one proton. A stable isotope is one which does not undergo radioactive decay. Deuterium was discovered as a natural occurring isotope in $H_2O$, which contains approximately 0.015% deuterium in the form of "heavy water" ($D_2O$). Its use as a moderator in nuclear reactors, initially provided impetus for its large-scale manufacture. However, all $D_2O$ production processes require large amounts of energy, so that its cost has remained high. Some of the physical properties of $D_2O$ include greater density and viscosity than $H_2O$ and a higher melting and boiling point; whereas differences in various other physical properties are less marked. The differences between a deuterated and parent compound, also called the protio molecule, is exploited in drug discovery programs through isotopic labeling techniques to better understand mechanism of action, as well as to identify and quantify metabolites in an effort to understand metabolism-mediated toxicities.

Stable isotope-labeled compounds have been employed in several areas of biomedical research. The combination of stable isotope-labeling techniques with mass spectrometry (MS), which allows rapid acquisition and interpretation of data, has promoted greater use of these stable isotope-labeled compounds in a number of fields including absorption, distribution, metabolism, and excretion (ADME) studies. The use of stable isotope labeling to study various aspects of the metabolism and pharmacokinetics of drugs and other foreign compounds in animals and humans has been well-documented. See, e.g., Zhu, M., et al., Detection and characterization of metabolites in biological matrices using mass defect filtering of liquid chromatography/high resolution mass spectrometry data. *Drug Metab. Dispos.* 34:1722-1733 (2006).

Compounds labeled with stable isotopes, such as deuterium and $^{13}$C, have been used effectively in the past by drug metabolism scientists and toxicologists to gain a better understanding of a drug's disposition and its potential role in target organ toxicities. Other quantitative applications of stable isotope-labeled compounds include studies conducted to distinguish in vivo and in vitro disposition of enantiomers where only one of the enantiomers was selectively labeled with stable isotopes. See, e.g., Eichelbaum, M., et al., Application of stable labeled drugs in clinical pharmacokinetic investigations. *Clin. Pharmacokinet.* 7:490-507 (1982). In another study, a stable isotope-labeled glucuronide conjugate of acetaminophen was used to explain the results of in vitro kinetic data. See, e.g., Mutlib, A. E., et al., Kinetics of acetaminophen glucuronidation by UDP Glucuronosyltransferases 1A1, 1A6, 1A9 and 2B15. Potential implications in acetaminophen-induced hepatotoxicity. *Chem. Res. Toxicol.* 19:701-709 (2006). Despite the greater availability of stable isotope-labeled compounds, drug metabolism scientists have yet to take full advantage of the potential use of these analogues for mechanistic metabolism and toxicity studies. These stable isotope-labeled compounds can be used to gain a better understanding of a drug's disposition and in toxicity studies. Identification of metabolite structures is very important, especially if one is trying to understand metabolism-mediated toxicities.

Toxicogenomics is a rapidly evolving field and is expected to play a very significant role in drug discovery and development in future. However, while significant progress has been made in toxicogenomics techniques, the interpretation of large sets of data produced from these studies can be a challenge. One approach that could be used to simplify interpretation of the data, especially from studies designed to link gene changes with the formation of reactive metabolites thought to be responsible for toxicities, is through the use of stable isotope-labeled compounds. The employment of analytical techniques, especially mass spectrometry and NMR used in conjunction with stable isotope-labeled compounds to establish and understand the mechanistic link between reactive metabolite formation, genomic and proteomic changes, and the onset of toxicity, appears very logical. This interdisciplinary approach may provide potential genomic and/or proteomic biomarkers of target organ toxicities, within the near future.

The greater availability of stable isotope-labeled analogues, especially synthesized to be used as internal standards for quantitative studies, has made it possible to use these compounds to conduct mechanistic metabolism studies. Often, a 1:1 mixture of labeled and unlabeled compound is used to create recognizable mass spectral ion patterns showing the presence of drug-related materials in complex biological mixtures. Technology has advanced to a point where a combination of mass spectrometry (MS) and stable isotope-labeled compounds can be used to provide a wealth of information on the metabolic disposition and identities of metabolites in the absence of radiolabeled compounds or authentic metabolite standards.

In addition, various other analytical techniques, such as nuclear magnetic resonance (NMR) spectroscopy, may be more widely used in conjunction with stable isotope-labeled compounds and mass spectrometry to better understand metabolic disposition and in elucidating structures of metabolites. Recent advancements in NMR technology that have allowed significant gains in sensitivity will make this methodology even more amenable in the determination of structures of metabolites of compounds labeled with stable isotopes. Strategic placement of stable isotope label(s) in a compound can also allow a better understand some of the gene changes attributed to reactive metabolite formation and/or to a particular metabolic pathway. Target organ toxicities can be modulated by selective introduction of stable isotopes, such as deuterium, in a molecule. Studying and comparing gene changes produced by labeled and nonlabeled compounds can provide an idea of critical genes that may be involved in the onset of toxicities. This is an area of intensive research, in the attempt to obtain "signature" genes that could be used as biomarkers for specific target organ toxicities.

Furthermore, one can use stable isotope-labeled compounds to delineate potential metabolism-mediated toxicities. If one suspects that a particular metabolic pathway or a metabolite is involved in causing toxicity by in situ generation of toxic metabolites as latently reactive species or "shunt-products" in vivo, stable isotope labels can be placed in such a manner by strategically substituting acidic protons by deuterium as to modulate the formation of the specific metabolite, hence potentially mitigating the toxicity. Obviously, one can conduct in vitro studies with labeled and nonlabeled compounds to understand the effect of labeling (e.g., the kinetic/deuterium isotope effect, which will be discussed infra) on the formation of a metabolite before an extensive toxicity study is conducted. Having stable isotope "labels" on reactive intermediates can greatly assist the identification of sites on proteins modified through covalent binding. Studies can be designed to investigate if particular proteins are targeted by reactive intermediates using stable isotope-labeled compounds. Studies encompassing the simultaneous use of radio- and stable isotope-labeled compounds to study proteomic and genomic changes as a consequence of reactive metabolite-mediated toxicity should potentially lead to a better understanding of some target organ toxicities and perhaps may lead to the identification of potential genomic or proteomic biomarkers.

Living systems exposed to $D_2O$ experience at least two sets of effects. One is a "solvent isotope effect", due to the properties of $D_2O$ itself, and especially its effects on the structure of water and macromolecules. The second is the "kinetic isotope effect" (KIE), resulting from the ability of $D_2O$ to replace H with D in biological molecules. In general, the C-D bond is about 10-times as strong as the C—H bond and is more resistant to chemical or enzymatic cleavage. Thus, compounds with C-D bonds tend to remain stable in $H_2O$ indefinitely, and such compounds have been very widely used for isotopic studies. O-D, N-D and S-D bonds are also stronger than the corresponding protonated forms, but the D in such bonds quickly exchanges with H in $H_2O$ especially when the deuterated position in the molecule is chemically labile for deuterium scrambling or rearrangements. See, e.g., Thomas, A. E 1971. Deuterium labeling in organic chemistry. Appleton-Century Crofts: New York. Deuterium isotope effects are usually considered in terms of D linkages to C atoms. Deuteration of O, N and S in biological molecules must occur rapidly when the cells are exposed to $D_2O$ but the reversibility of these processes by exchange with $H^+$ makes it very difficult to assess the biological effects of such deuteration. The ratio of the rates of cleavage of a C-protonated and D-deuterated compound, expresses the "primary" deuterium isotope effect, usually called simply the kinetic isotope effect (KIE). See, e.g., Foster, A. B., Deuterium isotope effects in the metabolism drugs and xenobiotics: implications for drug design. Adv. Drug Res. 14:1-40 (1985). Ten-fold differences in reaction rates are common.

"Secondary" deuterium isotope effects occur when attachment of deuterium to another atom affects the rate of C—H cleavage; such effects are usually small. The existence of a DIE in comparing protonated and deuterated compounds has been widely used to show whether metabolic reactions involve cleavage of $^{13}C$ bonds. For example, this technique was used by Deraaiyagala, et al., (β-Secondary and solvent deuterium kinetic isotope effects and the mechanisms of base- and acid-catalyzed hydrolysis of penicillanic acid. *J. Org. Chem.* 60:1619-1625 (1995)) and by Paterson, et al., (An antibody binding site on cytochrome C defined by hydrogen exchange and two dimensional MNMR. *Science* 249:755-759 (1990) to study the mechanisms of antigen-antibody reactions. The use of deuterium labels in many spectroscopic studies (for a review see, e.g., Kushner, D. J., et al., Biotechnological potential of heavy water and deuterated compounds. *Proceedings of Biotechnology Risk Assessment Symposium*. Ottawa, Canada. Jun. 13-15, 1996. Edited by Levin. C. and J. S. Angle. University of Maryland Biotechnology Institute Publication 1003. pp. 75-89 (1997)) illustrate the important contributions this isotope has made to current biological and pharmacological research. These aforementioned kinetic isotopic effects will be discussed more fully, below.

I. Deuterium Kinetic Isotope Effect

The deuterium kinetic isotope effect (KIE) is a dependence of the rate of a chemical reaction on the isotopic identity of an atom in a reactant and is observed in a change of the rate of reaction that occur when deuterium is substituted for hydrogen. By way of example, the KIE involving hydrogen and deuterium may be represented by the equation:

$$KIE = \frac{k_H}{k_D};$$

wherein $k_H$ and $k_D$ are reaction rate constants for hydrogen and deuterium, respectively.

The deuterium-mediated isotope effects result from the greater energy required to break a covalent bond to deuterium versus a covalent bond to hydrogen, and occur because of the significant mass difference between hydrogen and deuterium. The C-D bond is up to 10-times stronger than the C—H bond, making it more resistant to chemical or enzymatic cleavage. An isotopic substitution will greatly modify the reaction rate when the isotopic replacement is in a chemical bond that is broken or formed in the rate limiting step. In such a case, the change is termed a primary isotope effect. When the substitution is not involved in the bond that is breaking or forming, a smaller rate change, termed a secondary isotope effect is observed. Thus, the magnitude of the kinetic isotope effect can be used to elucidate the specific reaction mechanism. However, if other steps are partially rate-determining, the effect of isotopic substitution will be masked.

Isotopic rate changes are most pronounced when the relative mass change is greatest since the effect is related to vibrational frequencies of the affected bonds. For example, changing a hydrogen atom to deuterium represents a 100% increase in mass; whereas in replacing carbon-12 ($^{12}C$) with carbon-13 ($^{13}C$), the mass increases by only 8%. Therefore, the rate of a reaction involving a C—H bond is typically 6- to 10-times faster than the corresponding C-D bond. Moreover, the C-D bond is up to 10-times stronger than the C—H bond, making it more resistant to chemical or enzymatic cleavage. In contrast, a $^{12}C$ reaction is only approximately 1.04-times faster than the corresponding $^{13}C$ reaction (even though, in both cases, the isotope is one atomic mass unit heavier).

Isotopic substitution can modify the rate of reaction in a variety of ways. In many cases, the rate difference can be rationalized by noting that the mass of an atom affects the vibrational frequency of the chemical bond that it forms, even if the electron configuration is nearly identical. Heavier atoms will (in a classical mechanical analysis) lead to lower vibration frequencies or, in a quantum mechanical analysis, will have lower zero-point energy. The zero-point energy is the lowest possible energy that a quantum mechanical physical system can have, and is the energy of the ground state. With a lower zero-point energy, more energy must be supplied to break the bond, resulting in a higher activation energy for bond cleavage, which in turn lowers the measured rate. The rate of a chemical reaction may be calculated using, e.g., the Arrhenius equation.

The Arrhenius equation is a simple, but accurate, formula for the temperature dependence of the reaction rate constant, and therefore, the overall rate of a chemical reaction. In short, the Arrhenius equation gives the dependence of the rate constant "k" of a chemical reaction at the temperature "T" (in absolute temperature, such as degrees Kelvin or Rankine) and activation energy "$E_a$", as shown below:

$$k = Ae^{-a/RT};$$

wherein "A" is the pre-exponential factor or simply and "R" is the gas constant. The units of the pre-exponential factor are identical to those of the rate constant and will vary depending on the order of the reaction. If the reaction is first order it has the units $s^{-1}$, and for that reason it is often called the frequency factor or attempt frequency of the reaction. Most simply, k is the number of collisions which result in a reaction per second, A is the total number of collisions (leading to a reaction or not) per second and $e^{-E_a/RT}$ is the probability that any given collision will result in a reaction. When the activation energy is given in molecular units instead of molar units (e.g., joules) per molecule instead of joules per mole, the Boltzmann constant is used instead of the gas constant. It can be seen that either increasing the temperature or decreasing the activation energy (for example through the use of catalyst) will result in an increase in rate of reaction.

Given the small temperature range in which kinetic studies are carried, it is reasonable to approximate the activation energy as being independent of the temperature. Similarly, under a wide range of practical conditions, the weak temperature dependence of the pre-exponential factor is negligible compared to the temperature dependence of the $\exp(-E_a/RT)$ factor; except in the case of "barrierless" diffusion-limited reactions, in which case the pre-exponential factor is dominant and is directly observable.

The Arrhenius equation states that the fraction of molecules that have enough energy to overcome an energy barrier, that is, those with energy at least equal to the activation energy, depends exponentially on the ratio of the activation energy to thermal energy (RT), the average amount of thermal energy that molecules possess at a certain temperature. The transition state in a reaction is a short lived state (on the order of $10^{-14}$ sec) along the reaction pathway during which the original bonds have stretched to their limit. By definition, the activation energy ($E_a$) for a reaction is the energy required to reach the transition state of that reaction. Reactions that involve multiple steps will necessarily have a number of transition states, and in these instances, the activation energy for the reaction is equal to the energy difference between the reactants and the most unstable transition state. Once the transition state is reached, the molecules can either revert, thus reforming the original reactants, or new bonds form giving rise to the products. This dichotomy is possible because both pathways, forward and reverse, result in the release of energy. A catalyst facilitates a reaction process by lowering the activation energy leading to a transition state. Enzymes are examples of biological catalysts that reduce the energy necessary to achieve a particular transition state.

A carbon-hydrogen bond is by nature a covalent chemical bond. Such a bond forms when two atoms of similar electronegativity share some of their valence electrons, thereby creating a force that holds the atoms together. This force or bond strength can be quantified and is expressed in units of energy, and as such, covalent bonds between various atoms can be classified according to how much energy must be applied to the bond in order to break the bond or separate the two atoms. Bond strength is directly proportional to the absolute value of the ground-state vibrational energy of the bond. This vibrational energy, which is also known as the zero-point vibrational energy, depends on the mass of the atoms that form the bond. The absolute value of the zero-point vibrational energy increases as the mass of one or both of the atoms making the bond increases. Since deuterium (D) has twice the mass of hydrogen (H), it follows that a C-D bond is stronger than the corresponding C—H bond. Compounds with C-D bonds are frequently indefinitely stable in $H_2O$, and have been widely used for isotopic studies. If a C—H bond is broken during a rate-determining step in a chemical reaction (i.e., the step with the highest transition state energy), then substituting a deuterium for that hydrogen will cause a decrease in the reaction rate and the process will slow down. As previously discussed, this is known as the deuterium kinetic isotope effect (KIE). The magnitude of the KIE can be expressed as the ratio between the rates of a given reaction in which a C—H bond is broken, and the same reaction where deuterium is substituted for hydrogen. The KIE can range from about 1 (i.e., no isotope effect) to very large numbers (i.e., ≥50), meaning that the reaction can be fifty, or more, times slower when deuterium is substituted for hydrogen. High KIE values may be due in part to a phenomenon known as tunneling, which is a consequence of the uncertainty principle. Tunneling is ascribed to the small mass of a hydrogen atom, and occurs because transition states involving a proton can sometimes form in the absence of the required activation energy. Because deuterium has more mass than hydrogen, it statistically has a much lower probability of undergoing this phenomenon. Substitution of tritium for hydrogen results in yet a stronger bond than deuterium and gives numerically larger isotope effects.

If the cleavage of a C—H bond is implicated in the rate-determining step of a metabolic pathway, an overall decrease in metabolism will be observed when hydrogen is substituted with deuterium. Therefore, the reduction in metabolism attributable to deuterium substitution extends the desired effects of a drug while retarding its undesirable effects. One of the challenges of incorporating deuterium into a drug is the possibility of deuterium/hydrogen exchange within the physiological environment, which tends to eviscerate the effect of the compound. Further, when deuterium retards metabolism at one site, a phenomenon called "metabolic switching" or "metabolic shunting" can occur. The suppression of one metabolic pathway promotes metabolism at another site which quantitatively changes the paths of metabolism of the drug.

For a deuterated clinical candidate to be successful, it must address the problems of biochemical deuterium exchange and metabolic switching. The ideal starting point in developing a deuterated drug, also referred to as an isotopolog, is to selectively deuterate a drug in clinical development which has a known metabolic profile. Deuterated drugs of interest are those whose pharmacological or metabolic profiles differ from their protonated versions.

It should also be noted, however, that reactions are also known where the deuterated species reacts faster than the non-deuterated analog, and these cases are said to exhibit inverse kinetic isotope effects (IKIE). IKIEs are often observed in the reductive elimination of alkyl metal hydrides, e.g., $Me_2NCH_2CH_2NMe_2)PtMe(H)$. In such cases, the C-D bond in the transition state, an agostic species, is highly stabilized relative to the C—H bond.

II. Effects of $D_2O$ on Proteins, Cells and Tissues

As a solvent, $D_2O$ increases stability of proteins and other molecules, likely through increasing the formation of hydrophobic bonds. The effect of $D_2O$ on hydrophobic bond formation was thought to cause stabilization of heliozoan microtubule formation, and it has been used as an active polymerizer of tubulin in a number of systems. See, e.g., Sollott, S. J., et al., Taxol inhibits neointinal smooth muscle cell accumulation after angioplasty in the rat. *J. Clin. Invest.* 95 1869-1876 (1995).

The anti-mitotic action of $D_2O$ has stimulated its use as an antitumor agent. Effective $D_2O$ concentrations were usually too toxic to animals for rational chemotherapy. Combining $D_2O$ treatment with cytotoxic drugs such as methotrexate caused more reduction of tumor growth than either agent alone, although definitive cures did not result (Laissue, et al. 1982). A more recent study (Bauer, et al. 1995) showed that $D_2O$ was much more effective in killing malignant melanoma and carcinoma cells (colon carcinoma, glioblastoma, and small lung cell cancer cells) than PHA-stimulated lymphocytes and normal glial cells. For example, 90% $D_2O$ was shown to kill 70% of the former, but only 5% of the latter group. A differential effect on cell growth also occurred and 9 days of treatment with 90% $D_2O$ reduced the viable fraction of malignant cells to about 0.1%. Again. the effective $D_2O$ concentrations were too high for use in human therapy.

$D_2O$ inhibits mitosis in many plant and animal cells. This effect seems due partly to its effect on tubulin polymerization and also, or especially, on its action on microtubule organizing centers and other structures governing formation of the mitotic spindle (Lamprecht, et al. 1991). Other effects of $D_2O$ on cell structure have also been noted. In addition to affecting the formation of different blood cells, including platelets, $D_2O$ also affects platelets in vitro, inhibiting their spreading, retraction, and aggregation by ADP and collagen (Adains and Adanls 1988); as well as stimulating their adrenaline-induced aggregation (Reuter, et al. 1985). While these effects on platelet movement were discussed in terms of membrane receptors and energy metabolism, the effects of $D_2O$ on microfilament systems, which may be responsible for changes in shape of human neutrophil granulocytes (Zimmennann, et al. 1988), might also be involved in the effects on platelets.

Vasilescu and Karoila (1986) found that $D_2O$ inhibited bioelectrogenesis and contractility in nerve and muscle preparations and uncoupled electrical and mechanical functions in the isolated frog heart. It also lowered the ATP/ADP ratio in these tissues and also played an antagonistic role to anesthetics in sciatic nerve trunk. It was also shown that $D_2O$ only slightly inhibited sodium transport activity in human leucocytes. $D_2O$ competition may have important effects on calcium channel activity. It has been suggested that the antihypertensive effects of $D_2O$ may be related to its ability to reduce L-type calcium channel conductance in myocytes and calcium uptake in rat aortic rings treated with phenylephrine and KCl. $D_2O$ has a number of other effects on membrane function; including membrane depolarization and activation of calcium channels in algae, inhibition of $Na^+$—$K^+$ ATPase in membranes and interference with $H^+$ exchange in hepatic cells.

III. Effects of $D_2O$ on the Metabolism of Drugs

As previously stated, the C-D bond is more stable than the C—H bond, and once incorporated into organic compounds, deuterium is not readily exchangeable in $H_2O$. Deuterated organic compounds can be detected with great sensitivity by mass spectrometry and other methods. Because of these considerations, and the generally very low toxicity of deuterated compounds (especially compared with radioactive ones), such deuterated drugs are very widely used in studies of metabolism and movement of drugs and other substances in humans and other animals.

Deuteration of pharmaceuticals to improve pharmacokinetics (PK), pharmacodynamics (PD), and toxicity profiles, has been demonstrated previously with some classes of drugs. However, this method may not be applicable to all drug classes. For example, deuterium incorporation can lead to metabolic switching. The concept of metabolic switching asserts that xenogens, when sequestered by Phase I enzymes, may bind transiently and re-bind in a variety of conformations prior to the chemical reaction (e.g., oxidation). This hypothesis is supported by the relatively vast size of binding pockets in many Phase I enzymes and the promiscuous nature of many metabolic reactions. Metabolic switching can potentially lead to different proportions of known metabolites as well as altogether new metabolites. This new metabolic profile may impart more or less toxicity. Such pitfalls are non-obvious and are not predictable a priori for any drug class.

There are, however, multiple specific examples of deuterium's effect on the metabolism of biologically active molecules. For example, the anesthetic chloroform ($CHCl_3$) is metabolized in vivo to phosgene, a highly reactive alkylating agent. Deuteration of chloroform to deuterochloroform ($CDCl_3$) decreases its metabolic rate, thereby reducing liver and lung toxicity in rats by up to 70% over chloroform. Conversely, 1,2-dibromoethane ($ClCH_2CH_2Cl$) is itself a DNA alkylating species, and the tetra-deuterated analog ($ClCD_2CD_2Cl$) is found to be metabolized markedly more slowly than the protio version. However, the deuterated species actually causes more DNA damage than its protio counterpart because reduced metabolism prolongs the existence of the reactive species in the body.

Deuteration can also reduce a drug's pharmacological activity. An example is the anti-anxiety drug Valium® (diazepam), which requires 3-hydroxylation to oxepam for its anticonvulsive action. Diazepam, which is di-deuterated at position 3, has lower anticonvulsive action which may be due to the lower degree of 3-hydroxylation.

Deuterated analogs of various drugs including, but not limited to: the electron-affinic radiosensitizers and antitumor agents—RSU 1069 and Ro 03-8799; neurotoxill MPTP (1-inethyl-4-phenyl-1,2,3,6-tetrahydi-opyridine); nordiazepain; amines; nonsteroidal anti-inflammatory 2-arylpropionic acids; anti-malarial drugs; penicillamine; and the like have been synthesized and studied. For a more complete listing of various deuterated drugs, see, e.g., Yarnell, A., Heavy Hydrogen Drugs Turn Heads, Again. *Chem. Engineer. News* June 22:36-38 (2009).

Of special interest are drugs that are metabolized by the hepatic cytochrome P450 system, and the monooxygenases that act on various types of compounds. One of the first steps in all such reactions is the breaking of a C—H bond; and compounds that have C-D structures at the site of enzymatic attack are more resistant to P450-induced change. Resistance to P450-induced changes may lead to an increase in duration of pharmacological action or other desired properties. For example, tamoxifen is widely utilized in the treatment of human breast cancer, but it has also been shown to be capable of causing liver cancers in rats. This is thought to be related to a hydroxylation of part of the tamoxifen molecule, converting it to a DNA adduct. This hypothesis is supported by findings that deuterated tamoxifen, which has lower hepatotoxicity than the hydrogenated form, was also less susceptible to hydroxylation (Jarman et al. 1995).

Incorporating deuterium into novel compounds in an effort to mediate metabolism is a strategy which is finding success in traditional drug design and development. While deuterium has been extensively used as a tool to identify metabolites and metabolic pathways, it has only just recently been incorporated into several clinical candidates in Phase 1 drug development programs targeting deuterated analogs of small molecules in an effort to alter their metabolic profiles. Initial results from the clinical trials of deuterated Effexor® and Paxil® analogs, demonstrate the potential of deuterating known drugs, as both trials exhibited a reduction in the metabolism of the aforementioned deuterated compounds. See, Yarnell, A., Heavy Hydrogen Drugs Turn Heads, Again. *Chem. Engineer. News* June 22:36-38 (2009). More specifically, an example of the differences between an isotopolog and its protio version is shown in the clinical trial data of SD-254, an isotopolog of Effexor®. SD-254 was found to be metabolized half as fast as Effexor®, and pharmacologically-effective levels of the drug were maintained after 24 hours, substantially longer than that observed for the protio version. See, Id. This difference in the pharmacokinetics of SD-254 may allow for the administration of a lower dose while maintaining the same effects, thereby decreasing the incidences of deleterious side effects, which are generally dose-related.

It should be noted, however, that recent FDA guidance on the safety testing of metabolites will probably lead some investigators to revisit the application of stable isotope-labeled compounds in absorption, distribution, metabolism, and excretion (ADME) studies. The ability to demonstrate human-specific metabolite coverage in preclinical species as early as possible has become a challenge with the issuance of this guidance. Hence, identification of major human metabolites (considered to be greater than 10% of parent AUC values) during early drug development has become very important. The administration of a 1:1 mixture of labeled and nonlabeled analogues is one approach that will enable researchers and drug developers to rapidly identify all drug-related components in the plasma of humans during early stages of drug development. Even though major progress has been made in the field of mass spectrometry in detecting and identifying metabolites, one can still possibly miss unexpected or unusual metabolites using the existing LC/MS technology. The appearance of twin ion pairs in the mass spectra of plasma extracts can be used to scan for all possible metabolites in circulation in the absence of synthetic metabolite standards or radiolabeled compounds. Additionally, the application of LC-CRIMS (liquid chromatography-chemical reaction interface mass spectrometry) in combination with stable isotope-labeled compounds to obtain both qualitative and quantitative information on metabolites of potential therapeutic agents administered in early human studies also may be increasingly utilized.

SUMMARY OF THE INVENTION

The present invention described and claimed herein has many attributes and embodiments including, but not limited to, those set forth or described or referenced in this Summary section. However, it should be noted that this Summary is not intended to be all-inclusive, nor is the invention described and claimed herein limited to, or by, the features or embodiments identified in said Summary. Moreover, this Summary is included for purposes of illustration only, and not restriction.

The present invention discloses and claims novel compounds and method of synthesis thereof. These aforementioned novel compounds comprise deuterated analogs of (4S)-4-Ethyl-4-hydroxy-11-[2-(trimethylsilyl)ethyl]-1H-pyrano[3',4':6,7]indolizino[1,2-b]quinoline-3,14(4H,12H)-dione (also known as 7-[2-trimethylsilyl)ethyl]-20(S)-camptothecin; BNP1350; and Karenitecin®), and include, but are not limited to: (i) BNP 10120 (4S)-12,12-Dideutero-4-ethyl-4-hydroxy-11-[2-(trimethylsilyl)ethyl]-1H-pyrano[3',4':6,7]indolizino[1,2-b]quinoline-3,14(4H,12H)-dione; (ii) BNP10121 (S)-4-Ethyl-4-hydroxy-11-[1,1,2,2-tetradeutero-2-(trimethylsilyl)ethyl]-1H-pyrano[3',4':6,7]indolizino[1,2-b]quinoline-3,14(4H,12H)-dione, and (iii) pharmaceutically-acceptable salts and/or derivatives thereof. The present invention also discloses and claims formulations comprising one or more of the aforementioned novel compounds of the present invention, and the use of the disclosed compounds and formulations in methods of treating diseases and conditions that are beneficially treated by administering deuterated analogs of (4S)-4-Ethyl-4-hydroxy-11-[2-(trimethylsilyl)ethyl]-1H-pyrano[3',4':6,7]indolizino[1,2-b]quinoline-3,14(4H,12H)-dione (also known as 7-[2-trimethylsilyl)ethyl]-20(S)-camptothecin; BNP1350; and Karenitecin), and pharmaceutically-acceptable salts and/or derivatives thereof.

One embodiment of the invention discloses the administration of a formulation which contains a sufficient concentration of said novel deuterated Karenitecin® analog, pharmaceutically-acceptable salt and/or derivative thereof to provide a total dosage administration of about 0.1 mg/m$^2$ to about 100 mg/m$^2$. In a preferred embodiment, the novel deuterated Karenitecin® analog, pharmaceutically-acceptable salts and/or derivative thereof is dissolved, in the presence of a pharmaceutically-acceptable acid, in one or more solvents including, but not limited to, N-methylpyrrolidinone, dimethylisosorbide, or dimethylacetamide.

Another embodiment discloses a formulation comprising a sufficient concentration of said novel deuterated Karenitecin® analog, pharmaceutically-acceptable salt and/or derivative thereof to provide a total dosage administration of about 0.1 mg/m$^2$ to about 100 mg/m$^2$, and containing and from approximately 0.01 to approximately 0.9 part by weight of a pharmaceutically-acceptable organic carboxylic acid per part by weight of said novel deuterated Karenitecin® analog, pharmaceutically-acceptable salt and/or derivative thereof. In the most preferred embodiment the pharmaceutically-acceptable organic carboxylic acid is citric acid, or phosphoric acid.

One embodiment of the present invention discloses a formulation comprising a pharmaceutically-acceptable organic carboxylic acid which is from approximately 0.05 to approximately 0.1 part by weight of said novel deuterated Karenitecin® analog, pharmaceutically-acceptable salt and/or derivative thereof.

One embodiment discloses a formulation further comprising taurocholic acid, or a pharmaceutically-acceptable salt thereof, and polyethylene glycol.

Another embodiment discloses a formulation comprising for each part by weight of said novel deuterated Karenitecin® analog, pharmaceutically-acceptable salt and/or derivative thereof, approximately 1 to approximately 10 parts by weight of N-methylpyrrolidinone, dimethylisosorbide, or dimethylacetamide, approximately 0.005 to approximately 0.5 parts by weight of citric acid, approximately 1 to approximately 10 parts by weight of taurocholic acid, or a pharmaceutically-acceptable salt thereof, and approximately 1 to approximately 10 parts by weight of polyethylene glycol.

Another embodiment discloses a formulation comprising for each part by weight of said novel deuterated Karenitecin® analog; pharmaceutically-acceptable salt and/or derivative thereof, approximately 1 to approximately 10 parts by weight of N-methylpyrrolidinone, dimethylisosorbide, or dimethylacetamide, approximately 0.005 to approximately 0.5 parts by weight of a pharmaceutically-acceptable organic carboxylic acid, approximately 1 to approximately 10 parts by weight of taurocholic acid, or a pharmaceutically-acceptable salt thereof, approximately 1 to approximately 10 parts by weight of polyethylene glycol, approximately 0.1 to approximately 2 parts by weight of glycerin, approximately 0.1 to approximately 2 parts by weight of ethanol, and approximately 0.005 to approximately 0.5 parts of a buffer. In a preferred embodiment, the pharmaceutically-acceptable organic carboxylic acid is citric acid, the polyethylene glycol has a molecular weight of approximately 300.

Another embodiment discloses a formulation comprising a sufficient concentration of said novel deuterated Karenitecin® analog, pharmaceutically-acceptable salt and/or derivative thereof to provide a total dosage administration of about 0.1 mg/m$^2$ to about 100 mg/m$^2$, dissolved in approximately 1 to approximately 10 parts by weight of N-methylpyrrolidinone, dimethylisosorbide, or dimethylacetamide, in the presence of approximately 0.1 to approximately 0.5 parts by weight of a pharmaceutically-acceptable organic carboxylic acid, wherein said formulation further comprises approximately 5 to approximately 9 parts by weight of polyethylene glycol, approximately 0.1 to approximately 2.0 parts by weight of a pharmaceutically-acceptable alcohol, and approximately 1 to approximately 10 parts by weight of a non-ionic surfactant. In a preferred embodiment, the pharmaceutically-acceptable organic acid is citric acid, the polyethylene glycol has a molecular weight of approximately 300, the lower alcohol is ethanol, and wherein said surfactant is polysorbate-80 or poloxamer PF-127.

One embodiment discloses a method for the administration of a formulation comprising said novel deuterated Karenitecin® analog, pharmaceutically-acceptable salt and/or derivative thereof, to a previously untreated subject with cancer, comprising of infusing from approximately 0.1 mg/m$^2$ to approximately 100 mg/m$^2$ of said formulation over a duration of approximately 120 minutes given once per week for three consecutive weeks with 2 weeks rest after each 3 week cycle, wherein said formulation is sterilized and prepared for oral, intrapleural, intrathecal, intracisternal, intravesicular, intraperitoneal, topical or parenteral administration to a subject with cancer.

One embodiment discloses a method for the administration of a formulation comprising said novel deuterated Karenitecin® analog, pharmaceutically-acceptable salt and/or derivative thereof to a subject with cancer, comprising of infusing from approximately 0.1 mg/m$^2$ to approximately 75 mg/m$^2$ of said formulation over a duration of approximately 120 minutes given once per week for three consecutive weeks with 2 weeks rest after each 3 week cycle, wherein said formulation is sterilized and prepared for oral, intrapleural, intrathecal, intracisternal, intravesicular, intraperitoneal, topical or parenteral administration to a subject with cancer.

One embodiment discloses a method for the administration of a formulation comprising said novel deuterated Karenitecin® analog, pharmaceutically-acceptable salt and/or derivative thereof to a subject with cancer, comprising of infusing from approximately 0.1 mg/m$^2$ to approximately 50 mg/m$^2$ of said formulation over a duration of approximately 120 minutes given once per week for three consecutive weeks with 2 weeks rest after each 3 week cycle, wherein said formulation is sterilized and prepared for oral, intrapleural, intrathecal, intracisternal, intravesicular, intraperitoneal, topical or parenteral administration to a subject with cancer.

One embodiment discloses a method for the parenteral administration of a formulation comprising said novel deuterated Karenitecin® analog, pharmaceutically-acceptable salt and/or derivative thereof to a subject with cancer, said method comprising infusing from approximately 0.1 mg/m$^2$ to approximately 100 mg/m$^2$ of said formulation over a duration of approximately 120 minutes every 21 to 28 days.

One embodiment discloses a method for the parenteral administration of a formulation comprising said novel deuterated Karenitecin® analog, pharmaceutically-acceptable salt and/or derivative thereof to a subject with cancer, said method comprising infusing from approximately 0.1 mg/m$^2$ to approximately 75 mg/m$^2$ of said formulation over a duration of approximately 120 minutes every 21 to 28 days.

One embodiment discloses a method for the parenteral administration of a formulation comprising said novel deuterated Karenitecin® analog, pharmaceutically-acceptable salt and/or derivative thereof to a subject with cancer, said method comprising infusing from approximately 0.1 mg/m$^2$ to approximately 50 mg/m$^2$ of said formulation over a duration of approximately 120 minutes for three consecutive days every 21 to 28 days.

Another embodiment discloses a method for the parenteral administration of a said novel deuterated Karenitecin® analog, pharmaceutically-acceptable salt and/or derivative thereof, in combination with one or more chemotherapeutic agents, wherein said chemotherapeutic agents include, but are not limited to, a fluropyrimidine; a pyrimidine nucleoside; a purine nucleoside; an antifolate, a platinum analog; an anthracycline/anthracenedione; an epipodopodophyllotoxin; a camptothecin; a hormone, a hormonal analog; an antihormonal; an enzyme, protein, peptide, or antibody; a vinca alkaloid; a taxane; an epothilone; an antimicrotubule agent; an alkylating agent; an antimetabolite; a topoisomerase inhibitor; an antiviral; or another cytotoxic and cytostatic agent.

One embodiment discloses a method for the oral administration of a formulation comprising said novel deuterated Karenitecin® analog, pharmaceutically-acceptable salt and/or derivative thereof to a subject with cancer, said method consisting of administering from approximately 0.1 mg/m$^2$ to approximately 100 mg/m$^2$ of said formulation in single or divided dosages within a 24 hour period every 21 to 28 days.

One embodiment discloses a method for the oral administration of a formulation comprising said novel deuterated Karenitecin® analog, pharmaceutically-acceptable salt and/or derivative thereof to a subject with cancer, said method consisting of administering from approximately 0.1 mg/m$^2$ to approximately 75 mg/m$^2$ of said formulation daily in single or divided doses for three consecutive days every 21 to 28 days.

One embodiment discloses a method for the oral administration of a formulation comprising said novel deuterated Karenitecin® analog, pharmaceutically-acceptable salt and/or derivative thereof to a subject with cancer, said method consisting of administering from approximately 0.1 mg/m$^2$ to approximately 50 mg/m$^2$ of said formulation daily in single or divided doses for three consecutive days every 21 to 28 days.

Another embodiment discloses a method for the oral administration of a formulation comprising said novel deuterated Karenitecin® analog, pharmaceutically-acceptable salt and/or derivative thereof to a subject with cancer, said method consisting of administering from approximately 0.1 mg/m$^2$ to approximately 100 mg/m$^2$ of said formulation in single or divided dosages within a 24 hour period given once per week for three consecutive weeks with 2 weeks rest after each 3 week cycle.

One embodiment discloses a method for the oral administration of a formulation comprising said novel deuterated Karenitecin® analog, pharmaceutically-acceptable salt and/or derivative thereof to a previously untreated subject with cancer, said method consisting of administering from approximately 0.1 mg/m² to approximately 75 mg/m² of said formulation in single or divided doses within a 24 hour period once per week for three consecutive weeks with 2 weeks rest after each 3 week cycle.

Another embodiment discloses a method for the oral administration of a formulation comprising said novel deuterated Karenitecin® analog, pharmaceutically-acceptable salt and/or derivative thereof, said method consisting of administering from approximately 0.1 mg/m² to approximately 50 mg/m² of said formulation in single or divided dosages within a 24 hour period given once per week for three consecutive weeks with 2 weeks rest after each 3 week cycle.

One embodiment discloses a method for the oral administration of a formulation comprising said novel deuterated Karenitecin® analog, pharmaceutically-acceptable salt and/or derivative thereof to a subject with cancer, said method consisting of administering from approximately 0.1 mg/m²/day to approximately 100 mg/m²/day of said formulation in single or divided daily doses administered within each 24 hour period for two to five consecutive days and repeated every 21 to 48 days.

One embodiment discloses a method for the oral administration of a formulation comprising said novel deuterated Karenitecin® analog, pharmaceutically-acceptable salt and/or derivative thereof to a subject with cancer, said method consisting of administering from approximately 0.1 mg/m²/day to approximately 75 mg/m²/day of said formulation in single or divided daily doses administered within each 24 hour period for two to five consecutive days and repeated every 21 to 48 days.

One embodiment discloses a method for the oral administration of a formulation comprising said novel deuterated Karenitecin® analog, pharmaceutically-acceptable salt and/or derivative thereof to a subject with cancer, said method consisting of administering from approximately 0.1 mg/m²/day to approximately 50 mg/m²/day of said formulation in single or divided daily doses administered within each 24 hour period for two to five consecutive days and repeated every 21 to 48 days.

One embodiment discloses a method for the administration of a formulation comprising said novel deuterated Karenitecin® analog, pharmaceutically-acceptable salt and/or derivative thereof to a subject with one or more cancers who is also concomitantly suffering from hemorrhagic cystitis and renal toxicity.

In addition to disclosing methods for the synthesis of novel deuterated Karenitecin® analogs, the present invention also discloses pharmaceutically-acceptable formulations which may be utilized with said novel deuterated Karenitecin® analog, pharmaceutically-acceptable salt and/or derivative thereof. The formulation is adapted for administration by parenteral (e.g., intravenous) and/or oral routes to human subjects as treatment for various cancers/tumors. The formulation has as its active ingredient a pharmaceutically-effective amount of a said novel deuterated Karenitecin® analog, typically used in the treatment of cancers/tumors.

Specifically, the present invention involves the formulation and methods of use of the novel deuterated Karenitecin® analogs to treat cancer in subjects. In the case of intravenous administration of novel deuterated Karenitecin® analogs, several schedules and various dosages produce sufficient levels of said novel deuterated Karenitecin® analogs to yield beneficial chemotherapeutic effects in subjects, including humans.

Preferred formulations are disclosed in the Specification below, and do not limit the scope of the invention, which is defined by the Claims.

BRIEF DESCRIPTION OF THE FIGURES

FIG. 1: illustrates, in graphical form, the half maximal inhibitory concentration ($IC_{50}$) of BNP1350, BNP10120, and BNP10121 on wild-type (A2780/WT) and doxorubicin resistant (A2780/DX5) ovarian cancer cell lines. All of the aforementioned compounds were found to be effective inhibitors of cellular growth, with nanomolar $IC_{50}$ values.

DETAILED DESCRIPTION OF THE INVENTION

The preferred embodiments herein described are not intended to be exhaustive, or to limit the invention to the precise forms disclosed. They are chosen to best illustrate the principles of the invention, and its application and practical use to best enable others skilled in the art to follow its teachings.

DEFINITIONS

All definitions provided by: *Hawley's Condensed Chemical Dictionary*, 14$^{th}$ Edition, John Wiley & Sons, Inc., Publishers ((2001) and *American Hospital Formulary Service, Drug Information*, American Society of Health-System Pharmacists, Publishers (1999).

As used herein, the term "deuterium (D; $^2$H)", describes an isotope of hydrogen with a nucleus comprising one neutron and one proton. Deuterium is a stable isotope and does not undergo radioactive decay. It was discovered as a natural occurring isotope in $H_2O$, which contains approximately 0.015% deuterium in the form of "heavy water" ($D_2O$). The symbol "D", when used to represent a given position in a molecular structure, means that the specified position is enriched with deuterium above the naturally occurring distribution of deuterium. In an another embodiment deuterium enrichment is no less than about 10%, in another no less than about 50%, in another no less than about 90%, or in another no less than about 98% of deuterium at the specified position.

As utilized herein, the term "analog" or "structural analog" refers to a novel compound a having a structure similar to that of another one (i.e., the parent compound), but differing from it in respect to certain component(s). It can differ for the parent compound in one or more atoms, functional groups or substructures, which are replaced with other atoms, groups, or substructures. A structural analog can be imagined to be formed, at least theoretically, from the parent compound. Despite possess a high chemical similarity, structural analogs are not necessarily functional analogs, and can possess very different physical, chemical, biochemical, or pharmacological properties.

As utilized herein, the term "pharmaceutically-acceptable derivatives" refers to derivatives of the novel deuterated Karenitecin® analogs of the present invention, and include pharmaceutically-acceptable prodrugs, conjugates, hydrates, solvates, polymorphs, and/or tautomeric forms thereof.

As used herein, the term "deuterium enrichment" refers to the percentage of incorporation of deuterium at a given position in a molecule in the place of hydrogen. For example, deuterium enrichment of 1% at a given position means that 1% of molecules in a given sample contain deuterium at the specified position. Because the naturally occurring distribution of deuterium is about 0.0156%, deuterium enrichment at any position in a compound synthesized using non-enriched starting materials is about 0.0156%. The deuterium enrichment can be determined using conventional analytical methods known to one of ordinary skill in the art, including mass spectrometry (MS), nuclear magnetic resonance spectroscopy (NMR), and the like.

As used herein, the term "pharmaceutically-acceptable acid" is included in the solutions of the present invention. Any pharmaceutically acceptable acid may be used; for example mineral acids such as hydrochloric acid; and organic carboxylic acids, such as tartaric, citric, succinic, fumaric, or maleic acids. An organic carboxylic acid is preferred, and citric acid is most preferred. The amount of acid used may be from about 0.005 to about 0.5 parts by weight of acid per part by weight of a novel deuterated Karenitecin® analog and preferably from about 0.01 to 0.3 part by weight of acid per part by weight of a novel deuterated Karenitecin® analog. Citric acid is preferably used in a proportion of from about 0.05 to about 0.1, and about 0.1 part by weight in the presence of taurocholic acid or a pharmaceutically acceptable salt thereof.

As used herein, the term "subject" refers to an animal, including, but not limited to, a primate (e.g., human, monkey, chimpanzee, gorilla, and the like), rodents (e.g., rats, mice, gerbils, hamsters, ferrets, and the like), lagomorphs, swine (e.g., pig, miniature pig), equine, canine, feline, and the like. It should be noted, however, that the terms "subject" and "patient" are used interchangeably herein in reference, for example, to a mammalian subject, such as a human patient.

As utilized herein the term "cancer" refers to a class of diseases in which a group of cells display uncontrolled growth (i.e., division beyond the normal limits), invasion (i.e., intrusion on and destruction of adjacent tissues), and sometimes metastasis (i.e., spread to other location in the body via lymph or blood). Most cancers form a tumor but some, like leukemia, do not. Examples of cancer, include, but are not limited to, non-small cell lung cancer, adenocarcinoma, renal cell cancer, metastatic soft tissue sarcoma, ovarian cancer, fallopian tube cancer, primary peritoneal cancer, malignant glioma, neuroendocrine carcinoma, nasopharyngeal carcinoma, prostate cancer, and urothelial cancer, melanoma, breast cancer, prostatic carcinoma, kidney carcinoma, bladder carcinoma, pancreatic carcinoma, thyroid carcinoma, lung carcinoma, colon carcinoma, endometrial carcinoma, rectal carcinoma, brain carcinoma, liver carcinoma, and ovarian carcinoma. The term, as used herein, includes all known forms of cancer, including solid forms of cancer (e.g., tumors), lymphomas, and leukemias.

As used herein "anti-neoplastic agent" or "anti-cancer" or "chemotherapeutic agent" or "chemotherapy agent" refer to an agent that reduces, prevents, mitigates, limits, and/or delays the deleterious physiological manifestations, the growth or metastases of neoplasms, or by killing neoplastic cells directly by necrosis or apoptosis of neoplasms or any other mechanism. Chemotherapeutic agents include, for example, fluropyrimidines; pyrimidine nucleosides; purine nucleosides; anti-folates, platinum agents; anthracyclines/anthracenediones; epipodophyllotoxins; camptothecins; hormones; hormonal complexes; antihormonals; enzymes, proteins, peptides and polyclonal and/or monoclonal antibodies; vinca alkaloids; taxanes; epothilones; antimicrotubule agents; alkylating agents; antimetabolites; topoisomerase inhibitors; antivirals; and various other cytotoxic and cytostatic agents. "Chemotherapy" refers to treatments using recognized chemotherapeutic agents or chemotherapy agents.

As used herein, an "effective amount" or a "pharmaceutically-effective amount" in reference to the compounds or formulations of the instant invention refers to the amount sufficient to induce a desired biological, pharmacological, or therapeutic outcome in a subject with neoplastic disease. That result can be reduction, prevention, mitigation, delay, shortening the time to resolution of, alleviation of the signs or symptoms of, or exert a medically-beneficial effect upon the underlying pathophysiology or pathogenesis of an expected or observed side-effect, toxicity, disorder or condition, or any other desired alteration of a biological system.

As used herein "adverse symptom" means a manifestation or condition that is reported by the subject (e.g., pain, nausea, chills, depression, numbness, tingling, anorexia, dysguesia, and the like); whereas an "adverse sign" means an objective finding that is a physically observable manifestation of a condition, adverse event or disease in the subject (e.g., palpable purpura, maculopapular rash, spider angioma, Chvostek's sign, Babinski's sign, Trousseau's sign, opisthotonos, and the like).

The present invention discloses and claims novel compounds and method of synthesis thereof. These aforementioned novel compounds comprise deuterated analogs of (4S)-4-Ethyl-4-hydroxy-11-[2-(trimethylsilyl)ethyl]-1H-pyrano[3',4':6,7]indolizino[1,2-b]quinoline-3,14(4H,12H)-dione (also known as 7-[2-trimethylsilyl)ethyl]-20(S)-camptothecin; BNP1350; and Karenitecin®).

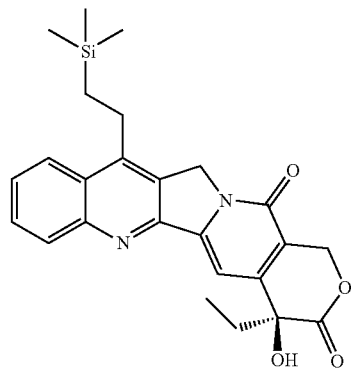

BNP1350

By way of example, and not of limitation, various examples of these novel deuterated analogs of Karenitecin® include, but are not limited to: (i) BNP10120 (4S)-12,12-Dideutero-4-ethyl-4-hydroxy-11-[2-(trimethylsilyl)ethyl]-1H-pyrano[3',4':6,7]indolizino[1,2-b]quinoline-3,14(4H,12H)-dione; (ii) BNP10121 (S)-4-Ethyl-4-hydroxy-11-[1,1,2,2-tetradeutero-2-(trimethylsilyl)ethyl]-1H-pyrano[3',4':6,7]indolizino[1,2-b]quinoline-3,14(4H,12H)-dione; and (iii) pharmaceutically-acceptable salts and/or derivatives thereof.

BNP10120 is a di-deuterated (at position C5) Karenitecin® analog having the following structural formula:

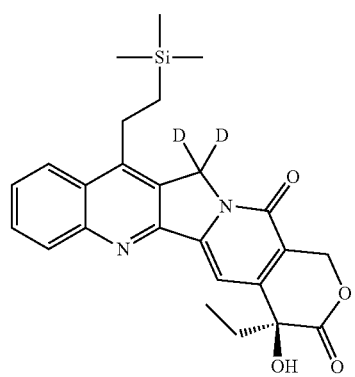

BNP10120

BNP10121 is a tetra-deuterated (at positions C22 and C23) Karenitecin® analog having the following structural formula:

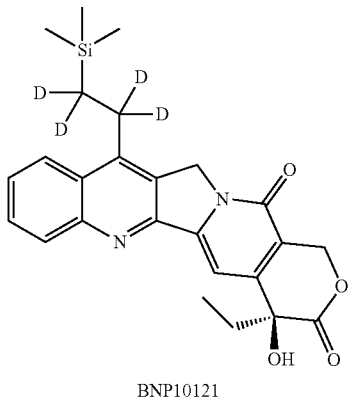

BNP10121

Specific Examples of the Synthetic Procedures Used for Deuterated Karenitecin® (BNP1350) Analogs It should be noted, that the hydrogen atoms bonded to C5, C22 and C23 of Karenitecin® are the most acidic protons found within the Karenitecin® (BNP1350) molecule. Hence, the replacement of carbon-hydrogen bonds with carbon-deuterium bonds at the C5, C22 and C23 positions of BNP1350 can potentially lead to a variety of beneficial pharmacological and physiological effects including, but not limited to, longer duration of action, improved safety profile, reduced levels of toxic metabolites, reduced inter-subject variability, and the like.

Synthesis of (4S)-12,12-Dideutero-4-ethyl-4-hydroxy-11-[2-(trimethylsilyl)ethyl]-1H-pyrano[3',4':6,7]indolizino[1,2-b]quinoline-3,14(4H,12H)-dione (BNP10120)

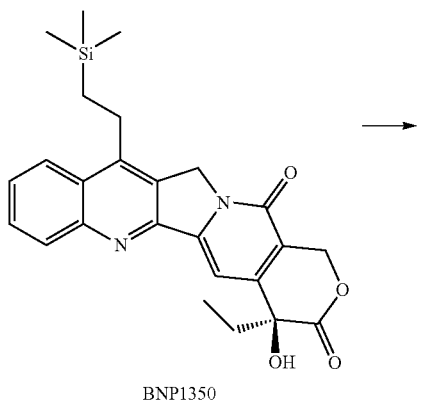

BNP1350

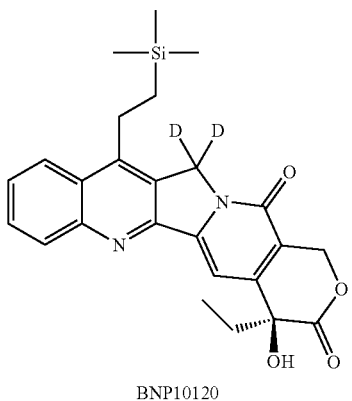 [SMILES: [2H]C1([2H])c2c(nc3ccccc3c2CC[Si](C)(C)C)-c2cc3c(c(=O)n21)COC(=O)[C@]3(O)CC]

BNP10120

BNP10120 was synthesized in the following manner. (4S)-4-Ethyl-4-hydroxy-11-[2-(trimethylsilyl)ethyl]-1H-pyrano[3',4':6,7]indolizino[1,2-b]quinoline-3,14(4H,12H)-dione (Karenitecin®, BNP1350; 110 mg) was dissolved in a mixed solvent of dichloromethane (3 ml) and methanol-d4 (3 mL). Ethyldiisopropylamine (Hunig's base; 0.5 mL) was added to the above solution in a sealed vial. The reaction mixture was then heated to 70° C. for two days, concentrated, and crystallized from dimethylformamide (DMF) to give 80 mg pale yellow crystalline powder (designated BNP 10120) with 72% yield. BNP10120 is a di-deuterated analog (at position C5) of BNP1350. The NMR spectra of BNP 10120 is given below:

$^1$H NMR (300 MHz, δ, CDCl$_3$) δ 8.23 (d, 1H, J=8.4 Hz), 8.03 (d, 1H, J=8.4 Hz); 7.78 (t, 1H, J=4.5 Hz), 7.66 (m, 2H), 5.76 (d, 1H, J=16.2 Hz), 5.31 (d, 1H, J=16.2 Hz), 3.70 (s, 1H), 3.08 (m, 2H), 1.87 (m, 2H), 0.98 (t, 3H, J=7.2 Hz), 0.90 (m, 2H), 0.14 (s, 9H). $^{13}$C NMR (300 MHz, δ, CDCl$_3$) δ 169.8, 153.6, 147.6, 146.1, 144.9, 143.6, 142.6, 126.4, 126.1, 123.7, 122.5, 122.0, 119.3, 119.1, 114.6, 94.4, 68.7, 62.2, 27.5, 20.1, 13.8, 3.9, −5.8.

Synthesis of 3-(trimethylsilyl)propionaldehyde_d4

To a solution of ethyl 3-(trimethylsilyl)propanoate_d4 (1.14 g) in 40 mL of dichloromethane was added diisobutylaluminium hydride (7 mL, 1 M in dichloromethane) dropwise for 40 minutes at −78° C. The reaction was then stirred for 3 hours at −78° C. Methanol (20 mL) and saturated potassium sodium tartrate solution (20 mL) were added to quench the reaction. The organic layer was washed with brine, dried over magnesium sulfate and concentrated under reduced pressure to dryness. The crude 3-(trimethylsilyl)propionaldehyde_d4 was then used directly for the synthesis of BNP10121, as set forth below.

Synthesis of (S)-4-Ethyl-4-hydroxy-11-[1,1,2,2-tetradeutero-2-(trimethylsilyl)ethyl]-1H-pyrano[3',4':6,7]indolizino[1,2-b]quinoline-3,14(4H,12H)-dione (BNP10121)

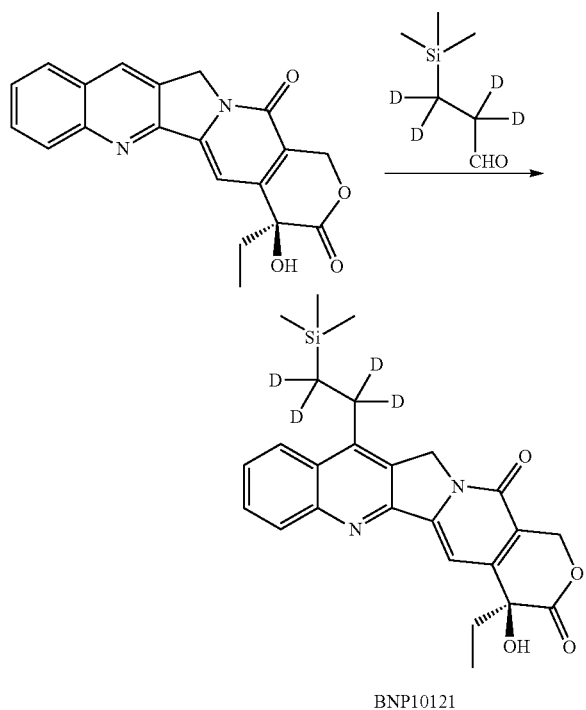

BNP10121

BNP10121 was synthesized in the following manner. To a slurry of ferrous sulfate heptahydrate (100 mg) in 30% sulfuric acid (2 mL), a solution of 3-(trimethylsilyl)propionaldehyde_d4 (153 mg) in 1,2-dimethoxyethane (2 mL) was introduced and the reaction mixture was stirred at room temperature. To the above reaction mixture, a solution of camptothecin (100 mg) in 30% sulfuric acid (8 mL) containing hydrogen peroxide (30%, 0.03 mL) was added dropwise during 10 minutes and the reaction mixture was stirred for 15 minutes. Finally, additional hydrogen peroxide (30%, 0.07 mL) was directly introduced into the reaction mixture and allowed to stir 3 hours. 30 mL of ice water was then added and the reaction mixture was extracted with chloroform (2×20 mL). The combined chloroform layer was washed once with process water (15 mL) and the layers were separated. The organic layer was then dried and concentrated under reduced pressure to dryness and the crude material was further purified on a pre-loaded 1 mm silica gel TLC plate using ethanol-dichloromethane mixture to obtain the pure product BNP10121. BNP10121 is a tetra-deuterated analog (at positions C22 and C23) of BNP1350. The NMR spectra of BNP10121 is provided below:

$^1$H NMR (300 MHz, $\delta$, CDCl$_3$) 8.24 (dd, 1H, J=8.1, 8.4 Hz), 8.05 (dd, 1H, J=0.9, 8.7 Hz), 7.86-7.80 (m, 1H), 7.71-7.65 (m, 2H), 5.77 (d, 1H, J=16.5 Hz), 5.32 (d, 1H, J=16.5 Hz), 5.25 (s, 2H), 1.98-1.88 (m, 2H), 1.05 (t, 3H, J=7.5 Hz), 0.188 (s, 9H).

Formulations and Methods of Administration

In addition, to disclosing novel deuterated Karenitecin® analogs and methods for their synthesis, the present invention also discloses and claims pharmaceutical formulations/compositions which may be utilized with said novel deuterated Karenitecin® analogs and their various pharmaceutically-acceptable salts and/or derivatives thereof. These formulations are efficacious for use with highly lipophilic camptothecin analogs such as the novel deuterated Karenitecin® analogs of the present invention and their various pharmaceutically-acceptable salts, and/or derivatives thereof.

By way of non-limiting example, the novel compositions and formulations of the present invention are adapted for: (i) oral (e.g., tablet, suspension, solution, gelatin capsule (hard or soft), sublingual, dissolvable tablet, troche, and the like), with sublingual administration avoiding first-pass metabolism through the liver; (ii) injection (e.g., subcutaneous administration, intradermal administration, subdermal administration, intramuscular administration, depot administration, intravenous administration, intra-arterial administration, and the like), wherein the administration may occur by, e.g., injection delivery, delivery via parenteral bolus, slow intravenous injection, and intravenous drip, and infusion devices (e.g., implantable infusion devices, both active and passive); (iii) intra-cavitary (e.g., into the intrapleural, intraperitoneal, intravesicular, and/or intrathecal spaces); and (iv) per rectum (e.g., suppository, retention enema) administration routes. The above-mentioned compositions and formulations include as their active ingredient one or more of said novel deuterated Karenitecin® analog, pharmaceutically-acceptable salt, and/or derivative thereof, as set forth herein.

Ideal properties of chemotherapeutic formulations include: (i) treatment, mitigation, and/or delay in progression, and/or improved survival of subjects with a neoplastic disease; (ii) an acceptably low level of chemotherapy-associated side-effects (with associated treatment interruptions, delays or dose modifications due to such side-effects); (iii) lack of interference with anti-tumor activity of other chemotherapeutic agents (which may be concomitantly administered) and overall lack of untoward drug-drug interactions; (iv) and efficacy in the form of medical benefit to the subject by increasing objective tumor response rate, increasing the time to tumor progression or the duration of tumor remission or disease stabilization, and improving overall subject survival.

A. Parenteral Formulations and Administration

Aspects of the invention include controlled or other doses, dosage forms, formulations, compositions and/or devices containing a novel deuterated Karenitecin® analog of the present invention and/or novel deuterated Karenitecin® analog, pharmaceutically-acceptable salt, derivative, prodrug, conjugate, hydrate, solvate, polymorph, and/or tautomeric form thereof, include, but are not limited to, doses and dosage forms for injection, (e.g., subcutaneous administration, subdermal administration, intramuscular administration, depot administration, intravenous administration (including delivery via bolus, slow intravenous injection, intravenous drip), and infusion devices (including implantable infusion devices, both active and passive).

Examples of dosage of forms suitable for injection of the compounds and formulations of the invention include delivery via bolus such as single or multiple administrations by intravenous injection, subcutaneous, subdermal, and intramuscular administration. These forms may be injected using syringes, pens, jet injectors, and internal or external pumps, for example. Needleless "jet injectors" are also known in the art and utilize a pneumatic "jet" of pressurized air to inject a fine spray of solution into the skin. See, e.g., *Pharmaceutical Dosage Forms: Parenteral Medications, Vol.* 1, *2nd ed*., Avis, et al., (Eds.), Mercel Dekker, New York, N.Y. (1992).

Infusion pumps, connected by flexible tubing to a catheter, which is inserted into the tissue just below the skin, are also known in the art. The catheter is left in place for several days at a time. The pump is programmed to dispense the necessary amount of solution at the proper times. Examples of implantable infusion devices for compounds, and formulations of the invention include any solid form in which the active agent is encapsulated within or dispersed throughout a biodegradable polymer or synthetic, polymer such as silicone, silicone rubber, silastic, or similar polymer.

Various examples of controlled drug formulations useful for delivery of the compounds and formulations of the invention are found in, e.g., Sweetman, S. C. (Ed.), Martindale. *The Complete Drug Reference,* 33*rd Edition*, Pharmaceutical Press, Chicago, pp. 2483 (2002); Aulton, M. E. (Ed.), Pharmaceutics. *The Science of Dosage Form Design*. Churchill Livingstone, Edinburgh, pp. 734 pp. (2000); and, Ansel, H. C., et al., *Pharmaceutical Dosage Forms and Drug Delivery Systems,* 7*th Ed*., Lippincott pp. 676 (1999). Excipients employed in the manufacture of drug delivery systems are described in various publications known to those skilled in the art including, for example, Kibbe, E. H., *Handbook of Pharmaceutical Excipients,* 3*rd Ed*., American Pharmaceutical Association, Washington, pp. 665 pp (2000).

Further examples of dosage forms of the invention include, but are not limited to modified-release (MR) dosage forms including delayed-release (DR) forms; prolonged-action (PA) forms; controlled-release (CR) forms; extended-release (ER) forms; timed-release (TR) forms; and long-acting (LA) forms. For the most part, these terms are used to describe orally administered dosage forms, however these terms may be applicable to any of the dosage forms, formulations, compositions and/or devices described herein. These formulations effect delayed total drug release for some time after drug administration, and/or drug release in small aliquots intermittently after administration, and/or drug release slowly at a controlled rate governed by the delivery system, and/or drug release at a constant rate that does not vary, and/or drug release for a significantly longer period than usual formulations.

Modified-release dosage forms of the invention include dosage forms having drug release features based on time, course, and/or location which are designed to accomplish therapeutic or convenience objectives not offered by conventional or immediate-release forms. See, e.g., Bogner, R. H., Bioavailability and bioequivalence of extended-release oral dosage forms. *U.S. Pharmacist* 22(Suppl.):3-12 (1997). Extended-release dosage forms of the invention include, for example, as defined by The United States Food and Drug Administration (FDA), a dosage form that allows a reduction in dosing frequency to that presented by a conventional dosage form, e.g., a solution or an immediate-release dosage form.

The present invention also envisions extended-release formulations containing a novel deuterated Karenitecin® analog of the present invention and/or a derivative thereof, for parenteral administration. Extending the rate of release and subsequent pharmacological activity of said novel deuterated Karenitecin® analog, pharmaceutically-acceptable salt, and/or derivative thereof, following injection may be achieved in a number of ways including, but not limited to, crystal or amorphous forms having prolonged dissolution characteristics; slowly dissolving chemical complexes of the camptothecin formulation; solutions or suspensions of said novel deuterated Karenitecin® analog, pharmaceutically-acceptable salt, and/or derivative thereof, in slowly absorbed carriers or vehicles (e.g., as oleaginous); increased particle size of said novel deuterated Karenitecin® analog in suspension; or, by injection of slowly eroding microspheres of said novel deuterated Karenitecin® analog, pharmaceutically-acceptable salt, and/or derivative thereof, (see, e.g., Friess, W., et al., Insoluble collagen matrices for prolonged delivery of proteins. *Pharmaceut. Dev. Technol.* 1:185-193 (1996)). For example, the duration of action of the various forms of insulin is based in part on its physical form (amorphous or crystalline), complex formation with added agents, and its dosage form (solution of suspension).

Carriers or excipients can also be used to facilitate administration of the compositions and formulations of the present invention. Examples of carriers and excipients include calcium carbonate, calcium phosphate, various sugars such as lactose, glucose, or sucrose, or types of starch, cellulose derivatives, gelatin, polyethylene glycols and physiologically compatible solvents. It may also be desirable to add suitable dispersing or suspending agents to the pharmaceutical formulation. These may include, for example, aqueous suspensions such as synthetic and natural gums, e.g., tragacanth, acacia, alginate, dextran, sodium carboxymethylcellulose, methylcellulose, polyvinyl-pyrrolidone or gelatin.

It is possible that various other ingredients may also be utilized in the parenteral pharmaceutical formulation of the present invention. Such additional ingredients may include wetting agents, oils (e.g., a vegetable oil such as sesame, peanut or olive), analgesic agents, emulsifiers, antioxidants, bulking agents, tonicity modifiers, metal ions, oleaginous vehicles, proteins (e.g., human serum albumin, gelatin or proteins) and a zwitterion (e.g., an amino acid such as betaine, taurine, arginine, glycine, lysine and histidine). Such additional ingredients, of course, should not adversely affect the overall stability of the pharmaceutical formulation of the present invention.

In addition to the above means of achieving extended drug action, the rate and duration of delivery of said novel deuterated Karenitecin® analog, pharmaceutically-acceptable salt, and/or derivative thereof, may be controlled by, for example by using mechanically controlled drug infusion pumps. The present invention in part provides infusion dose delivery formulations and devices, including but not limited to implantable infusion devices for delivery of compositions and formulations of the invention. Implantable infusion devices may employ inert material such as biodegradable polymers listed above or synthetic silicones, for example, cylastic, silicone rubber or other polymers manufactured by the Dow-Corning Corporation. The polymer may be loaded with the novel deuterated Karenitecin® analog, pharmaceutically-acceptable salt, and/or derivative thereof, and any excipients. Implantable infusion devices may also comprise a coating of, or a portion of, a medical device wherein the coating comprises the polymer loaded with the novel deuterated Karenitecin® analog, pharmaceutically-acceptable salt, and/or derivative thereof, and any excipients. Such an implantable infusion device may be prepared, e.g., as disclosed in U.S. Pat. No. 6,309,380, by coating the device with an in vivo biocompatible and biodegradable or bioabsorbable or bioerodable liquid or gel solution containing a polymer with the solution comprising a desired dosage amount of the novel deuterated Karenitecin® analog, pharmaceutically-acceptable salt, and/or derivative thereof, and any excipients. The solution is converted to a film adhering to the medical device thereby forming the implantable novel deuterated Karenitecin® analog-deliverable medical device.

An implantable infusion device may also be prepared by the in situ formation of a novel deuterated Karenitecin® analog-containing solid matrix as disclosed in U.S. Pat. No. 6,120,789, herein incorporated in its entirety. Implantable infusion devices may be passive or active. An active implantable infusion device may comprise: (i) a novel deuterated Karenitecin® analog and/or derivative thereof reservoir; (ii) a means of allowing the novel deuterated Karenitecin® analog, pharmaceutically-acceptable salt, and/or derivative thereof to exit said reservoir (e.g., through a semi-permeable membrane); and (iii) a "driving force" to propel the novel deuterated Karenitecin® analog pharmaceutically-acceptable salt, and/or derivative thereof from said reservoir. Such an active implantable infusion device may additionally be activated by an extrinsic signal, such as that disclosed in, e.g., WO 02/45779, wherein the implantable infusion device comprises a system configured to deliver said novel deuterated Karenitecin® analog, pharmaceutically-acceptable salt, and/or derivative thereof, wherein said infusion device comprises an external activation unit which is operable by the user to request activation of the implantable infusion device, including a controller to reject such a request prior to the expiration of a lockout interval. Examples of an active implantable infusion device include implantable drug pumps. Implantable drug pumps include, for example, miniature, computerized, programmable, refillable drug delivery systems with an attached catheter that inserts into a target organ system, usually the spinal cord or a vessel. See, e.g., Medtronic Inc. Publications: UC9603124EN NP-2687, 1997; UC199503941b EN NP-2347 182577-101,2000; UC199801017a EN NP3273a 182600-101, 2000; UC200002512 EN NP4050, 2000; UC199900546bEN NP-3678EN, 2000. Minneapolis, Minn.: Medtronic, Inc (1997-2000). Many pumps have 2 ports—one into which drugs can be injected and the other that is connected directly to the catheter for bolus administration or analysis of fluid from the catheter. Implantable drug infusion pumps (e.g., SynchroMed EL and SynchroMed Programmable Pumps; manufactured by Medtronic) are indicated for long-term intrathecal infusion of morphine sulfate for the treatment of chronic intractable pain; intravascular infusion of floxuridine for treatment of primary or metastatic cancer; intrathecal injection (e.g., baclofen injection) for severe spasticity; long-term epidural infusion of morphine sulfate for treatment of chronic intractable pain; long-term intravascular infusion of doxorubicin, cisplatin, or methotrexate for the treatment or metastatic cancer; and long-term intravenous infusion of clindamycin for the treatment of osteomyelitis. Such pumps may also be used for the long-term infusion of said novel deuterated Karenitecin® analog, pharmaceutically-acceptable salt, and/or derivative thereof, either at a desired concentration, for a desired number of doses, or steady-state administration. One form of a typical implantable drug infusion pump (e.g., SynchroMed EL Programmable Pump; Medtronic) is titanium covered and roughly disk shaped (measuring 85.2 mm in diameter, 22.86 mm in thickness and weighing a total of 185 grams), has a drug reservoir which holds a total liquid volume of 10 mL, and runs on a lithium thionyl-chloride battery with a 6- to 7-year life, depending upon amount of use. The downloadable memory contains programmed drug delivery parameters and calculated amount of drug remaining, which can be compared with actual amount of drug remaining to access accuracy of pump function, but actual pump function over time is not recorded. The pump is usually implanted in the right or left abdominal wall. Other pumps useful in the invention include, for example, portable disposable infuser pumps (PDIPs). Additionally, implantable infusion devices may employ liposome delivery systems, such as a small unilamellar vesicles, large unilamellar vesicles, and multilamellar vesicles can be formed from a variety of phospholipids, such as cholesterol, stearyl amine or phosphatidylcholines.

The present invention in part also provides for the formulation of said novel deuterated Karenitecin® analog, pharmaceutically-acceptable salt, and/or derivative thereof, in a microemulsion to enhance bioavailability. A microemulsion is a fluid and stable homogeneous solution composed of four major constituents, comprising: (i) a hydrophilic phase; (ii) a lipophilic phase; (iii) at least one surfactant (SA) and (iv) at least one cosurfactant (CoSA). A surfactant is a chemical compound possessing two groups, the first polar or ionic, which has a great affinity for water, the second which contains a longer or shorter aliphatic chain and is hydrophobic. These chemical compounds having marked hydrophilic character are intended to cause the formation of micelles in aqueous or oily solution. Examples of suitable surfactants include mono-, di- and triglycerides and polyethylene glycol (PEG) mono- and diesters. A cosurfactant, also known as a "co-surface-active agent", is a chemical compound having hydrophobic character, intended to cause the mutual solubilization of the aqueous and oily phases in a microemulsion. Examples of suitable co-surfactants include ethyl diglycol, lauric esters of propylene glycol, oleic esters of polyglycerol, and related compounds.

In the preferred formulation/compositions of the present invention, the preferred solvents include N-methylpyrrolidinone (NMP), dimethylacetamide (DMA), and/or dimethylisosorbide (DMI); or a combination of two or more of the aforementioned solvents being utilized as co-solvents. The most preferred solvent is NMP, a combination of NMP and DMA as co-solvents, or DMA as the primary co-solvent.

Preferred surfactants include, but are not limited to, polysorbates; with the most preferred surfactant being polysorbate 80. Preferred alcohols include, but are not limited to, ethyl alcohol and benzyl alcohol; with the most preferred alcohol being denatured ethyl alcohol. The preferred low molecular weight polyethylene glycols (PEGS), include but are not limited to, PEG 100, PEG 200, PEG 300, PEG 400, PEG 600, PEG 800; with the most preferred PEG being PEG 300.

A preferred embodiment of the present invention is a formulation comprising said novel deuterated Karenitecin® analog, pharmaceutically-acceptable salt, and/or derivative thereof, dissolved in N-methylpyrrolidinone (NMP), or dimethylisosorbide (DMI) and/or dimethylacetamide (DMA), alone or in combination, in the presence of a pharmaceutically-acceptable acid. An additional embodiment of the claimed invention is where the pharmaceutically-acceptable acid is an organic carboxylic acid, with the most preferred being citric acid. In another embodiment of the claimed invention, the solution of said novel deuterated Karenitecin® analog, pharmaceutically-acceptable salt, and/or derivative thereof, contains from about 0.1 mg to about 100 mg of the novel deuterated Karenitecin® analog, pharmaceutically-acceptable salt, and/or derivative thereof per mL of solution. This concentration would be effective for both oral and parenteral administration of said novel deuterated Karenitecin® analog, pharmaceutically-acceptable salt, and/or derivative thereof.

The novel deuterated Karenitecin® analog solution is prepared by dissolving the desired components in N-methylpyrrolidinone (NMP), dimethylisosorbide (DMI) and/or dimethylacetamide (DMA). Dimethylisosorbide has been used as solvent for muscle relaxants (see, e.g., U.S. Pat. No. 3,699, 230), tetracyclines (U.S. Pat. No. 3,219,529), aspirin (U.S. Pat. No. 4,228,162), and steroids (U.S. Pat. No. 4,082,881). NMP, DMI, and DMA have very good toxicity profiles and are miscible with ethanol, propylene glycol, isopropyl myristate, water, diethyl ether, corn oil, acetone, cottonseed oil, and the like.

The present invention is prepared by dissolving the desired components in NMP, DMI and/or DMA and the resulting solution is then filtered and the filtrate collected. The amount of the novel deuterated Karenitecin® analog contained in the solution of this invention is not specifically restricted, but may be any amount convenient for pharmaceutical purposes, and may be selected according to the dosage to be prepared. A preferred capsule filling solution contains a sufficient concentration of said novel deuterated Karenitecin® analog, pharmaceutically-acceptable salt, and/or derivative thereof, so as to provide a total dose of about 0.1 mg/m$^2$ to 100 mg/m$^2$.

As a preferred embodiment of the claimed invention, the novel deuterated Karenitecin® analog solution is prepared by dissolving the desired components in N-methylpyrrolidinone (NMP), dimethylisosorbide (DMI) and/or dimethylacetamide (DMA) in the presence of a pharmaceutically-acceptable acid. As previously defined, a pharmaceutically-acceptable acid is included in the solutions of the present invention. Any pharmaceutically acceptable acid may be used; for example mineral acids such as hydrochloric acid; and organic carboxylic acids, such as tartaric, citric, succinic, fumaric, or maleic acids. An organic carboxylic acid is preferred, and citric acid is most preferred, as well as phosphoric acid. The amount of acid used may be from about 0.005 to about 0.5 parts by weight of acid per part by weight of said novel deuterated Karenitecin® analog, pharmaceutically-acceptable salt, and/or derivative thereof, and preferably from about 0.01 to 0.3 part by weight of acid per part by weight of said novel deuterated Karenitecin® analog, pharmaceutically-acceptable salt, and/or derivative thereof. Citric acid is preferably used in a proportion of from about 0.05 to about 0.1, and about 0.1 part by weight in the presence of taurocholic acid or a pharmaceutically-acceptable salt thereof.

In the formulations provided by the instant invention, the said novel deuterated Karenitecin® analog, pharmaceutically-acceptable salt, and/or derivative thereof, is both soluble and the pH-labile E-ring is maintained in its active "closed" lactone-stable form. The non-enzymatic conversion of the pH labile E-ring from the "closed" lactone (i.e., active) to the "open" carboxylate form (i.e., inactive) is reduced by formulating the novel deuterated Karenitecin® analog under acidic pH conditions (<5.0). Thus, a water soluble acid is included to assure that an acidic pH value is maintained upon dilution to form the micellar solution. Examples of preferred solid water-soluble organic carboxylic acids effective in the present invention include, but are not limited to, citric, gluconic, maleic, tartaric, or ascorbic acids. Other acids may be also employed, but citric and phosphoric acid are most preferred.

The present invention also discloses and claims formulations comprising one or more of the aforementioned novel deuterated Karenitecin® analogs, and the use of the disclosed compounds and formulations in methods of treating diseases and conditions that are beneficially treated by administering Karenitecin® analogs, pharmaceutically-acceptable salts, and/or derivatives thereof.

One embodiment of the present invention is a method of administration of one or more of the aforementioned novel deuterated Karenitecin® analogs to a subject with cancer comprising infusing a fixed amount of one or more of said novel deuterated Karenitecin® analogs, pharmaceutically-acceptable salt, and/or derivative thereof, over a period of time and repeated at predetermined intervals.

Another embodiment of the invention discloses the administration of a formulation which contains a total dose of approximately 0.1 mg/m$^2$ to approximately 100 mg/m$^2$ of said novel deuterated Karenitecin® analog, pharmaceutically-acceptable salt, and/or derivative thereof. In a preferred embodiment, the deuterated Karenitecin® analog is dissolved, in the presence of a pharmaceutically-acceptable acid, in one or more solvents including, but not limited to, N-methylpyrrolidinone, dimethylisosorbide, or dimethylacetamide.

One embodiment discloses a formulation comprising a total dose of approximately 0.1 mg/m$^2$ to approximately 100 mg/m$^2$ of said novel deuterated Karenitecin® analog, pharmaceutically-acceptable salt, and/or derivative thereof, and containing and from approximately 0.01 to approximately 0.9 part by weight of a pharmaceutically-acceptable organic carboxylic acid per part by weight of said novel deuterated Karenitecin® analog, pharmaceutically-acceptable salt, and/or derivative thereof. In the most preferred embodiment the pharmaceutically-acceptable organic carboxylic acid is citric acid.

One embodiment of the present invention discloses a formulation comprising a pharmaceutically-acceptable organic carboxylic acid which is from approximately 0.05 to approximately 0.1 part by weight of said novel deuterated Karenitecin® analog, pharmaceutically-acceptable salt, and/or derivative thereof.

One embodiment discloses a formulation further comprising taurocholic acid, or a pharmaceutically-acceptable salt thereof, and polyethylene glycol.

Another embodiment discloses a formulation comprising for each part by weight of said novel deuterated Karenitecin® analog, pharmaceutically-acceptable salt, pharmaceutically-acceptable salt, and/or derivative thereof, approximately 1 to approximately 10 parts by weight of N-methylpyrrolidinone, dimethylisosorbide, or dimethylacetamide, approximately 0.005 to approximately 0.5 parts by weight of citric acid, approximately 1 to approximately 10 parts by weight of taurocholic acid, or a pharmaceutically-acceptable salt thereof, and approximately 1 to approximately 10 parts by weight of polyethylene glycol.

Another embodiment discloses a formulation comprising for each part by weight of said novel deuterated Karenitecin® analog, pharmaceutically-acceptable salt, and/or derivative thereof, approximately 1 to approximately 10 parts by weight of N-methylpyrrolidinone, dimethylisosorbide, or dimethylacetamide, approximately 0.005 to approximately 0.5 parts by weight of a pharmaceutically-acceptable organic carboxylic acid, approximately 1 to approximately 10 parts by weight of taurocholic acid, or a pharmaceutically-acceptable salt thereof, approximately 1 to approximately 10 parts by weight of polyethylene glycol, approximately 0.1 to approximately 2 parts by weight of glycerin, approximately 0.1 to approximately 2 parts by weight of ethanol, and approximately 0.005 to approximately 0.5 parts of a buffer. In a preferred embodiment, the pharmaceutically-acceptable organic carboxylic acid is citric acid, the polyethylene glycol has a molecular weight of approximately 300.

Another embodiment discloses a formulation comprising at total does of approximately 0.1 mg/m$^2$ to approximately 100 mg/m$^2$ of said novel deuterated Karenitecin® analog, pharmaceutically-acceptable salt, and/or derivative thereof, dissolved in approximately 1 to approximately 10 parts by weight of N-methylpyrrolidinone, dimethylisosorbide, or dimethylacetamide, in the presence of approximately 0.1 to approximately 0.5 parts by weight of a pharmaceutically-acceptable organic carboxylic acid, wherein said formulation further comprises approximately 5 to approximately 9 parts by weight of polyethylene glycol, approximately 0.1 to approximately 2.0 parts by weight of a pharmaceutically-acceptable alcohol, and approximately 1 to approximately 10 parts by weight of a non-ionic surfactant. In a preferred embodiment, the pharmaceutically-acceptable organic acid is citric or phosphoric acid, the polyethylene glycol has a molecular weight of approximately 300, the lower alcohol is ethanol, and wherein said surfactant is polysorbate-80 or poloxamer PF-127.

Other embodiments of the invention discloses a method where said novel deuterated Karenitecin® analog, pharmaceutically-acceptable salt, and/or derivative thereof, is infused into a subject with cancer, wherein said novel deuterated Karenitecin® analog, pharmaceutically-acceptable salt, and/or derivative thereof, is dissolved in N-methylpyrrolidinone (NMP) in the presence of a pharmaceutically-acceptable acid; said novel deuterated Karenitecin® analog, pharmaceutically-acceptable salt, and/or derivative thereof, is dissolved in dimethylisosorbide (DMI) in the presence of a pharmaceutically-acceptable acid; said novel deuterated Karenitecin® analog, pharmaceutically-acceptable salt, and/or derivative thereof, is dissolved in dimethylacetamide (DMA) in the presence of a pharmaceutically-acceptable acid. An object of the present invention is to provide a solution of the novel deuterated Karenitecin® analog in a NMP-, DMI- and/or DMA-containing solution. It should be noted that the solution may be formulated for parenteral use providing a useful and practical means to dissolve the drug or, as a concentrated solution, useful as a filling solution for oral gelatin capsules or rectal suppositories.

A preferred embodiment of the present invention is an formulation comprising a solution of said novel deuterated Karenitecin® analog, pharmaceutically-acceptable salt, and/or derivative thereof, dissolved in N-methylpyrrolidinone (NMP), dimethylisosorbide and/or dimethylacetamide containing a sufficient concentration of the novel deuterated Karenitecin® analog to provide a total dosage of about 0.1 mg/m$^2$ to about 100 mg/m$^2$ and containing from about 0.01 to about 0.9 part by weight of a pharmaceutically-acceptable organic carboxylic acid per part by weight of the novel deuterated Karenitecin® analog, pharmaceutically-acceptable salt, and/or derivative thereof It is more preferable to use approximately 0.01 to approximately 0.2 part by weight of a pharmaceutically-acceptable organic carboxylic acid per part by weight of the novel deuterated Karenitecin® analog, pharmaceutically-acceptable salt, and/or derivative thereof.

An additional embodiment of the present invention is wherein said part by weight of the pharmaceutically-acceptable organic carboxylic acid is from approximately 0.05 to approximately 0.1 part by weight per part by weight of the novel deuterated Karenitecin® analog, pharmaceutically-acceptable salt, and/or derivative thereof, and said organic carboxylic acid is citric acid.

Another embodiment of the invention is an formulation comprising a solution of the novel deuterated Karenitecin® analog, pharmaceutically-acceptable salt, and/or derivative thereof, dissolved in N-methylpyrrolidinone, dimethylisosorbide and/or dimethylacetamide in the presence of a pharmaceutically-acceptable acid, wherein said solution further comprises taurocholic acid or a pharmaceutically-acceptable salt thereof, and polyethylene glycol.

Yet another embodiment of the present invention is wherein the solution of formulation contains for each part by weight of the novel deuterated Karenitecin® analog, pharmaceutically-acceptable salt, and/or derivative thereof, approximately 1 to approximately 10 parts by weight of N-methylpyrrolidinone, dimethylisosorbide and/or dimethylacetamide, approximately 0.005 to approximately 0.5 parts by weight of a pharmaceutically-acceptable acid, approximately 1 to approximately 10 parts by weight of taurocholic acid or a pharmaceutically-acceptable salt thereof, and approximately 1 to approximately 10 parts by weight of polyethylene glycol. An additional embodiment is wherein said acid is an organic carboxylic acid, most preferably citric acid, or phosphoric acid.

Another embodiment of the claimed invention is the formulation further comprises a lower alcohol. Many different alcohols would be effective in the present invention, but most preferably, ethanol. Another embodiment of the claimed invention is the formulation further comprises glycerin as a co-solvent.

Yet another embodiment of the invention is an formulation comprising a solution of the novel deuterated Karenitecin® analog, pharmaceutically-acceptable salt, and/or derivative thereof, dissolved in N-methylpyrrolidinone, dimethylisosorbide and/or dimethylacetamide in the presence of a pharmaceutically-acceptable acid, wherein said solution further comprises taurocholic acid or a pharmaceutically-acceptable salt thereof, polyethylene glycol, ethanol, glycerin, and a buffer, such as sodium acetate, to maintain an acidic pH.

An additional embodiment of the present invention is wherein said solution contains for each part by weight of the novel deuterated Karenitecin® analog, pharmaceutically-acceptable salt, and/or derivative thereof, approximately 1 to approximately 10 parts by weight of N-methylpyrrolidinone, dimethylisosorbide and/or dimethylacetamide, approximately 0.005 to approximately 0.5 parts by weight of a pharmaceutically-acceptable acid, approximately 1 to approximately 10 parts by weight of taurocholic acid, or a pharmaceutically-acceptable salt thereof, approximately 1 to approximately 10 parts by weight of polyethylene glycol, approximately 0.1 to approximately 2 parts by weight of glycerin, approximately 0.1 to approximately 2 parts by weight of ethanol, and approximately 0.005 to approximately 0.5 parts of a buffer.

Another embodiment of the invention is wherein said polyethylene glycol has a molecular weight of about 300, and the formulation further comprises a non-ionic surfactant. Many different surfactants would be effective in the present invention, the poloxamer, PF-127, is most preferred.

Yet another embodiment of the invention is an formulation comprising a solution of the novel deuterated Karenitecin® analog, pharmaceutically-acceptable salt, and/or derivative thereof, dissolved in dimethylisosorbide or dimethylacetamide in the presence of a pharmaceutically-acceptable acid, wherein said solution further comprises a lower alcohol, polyethylene glycol, and surfactant. As a more preferred embodiment for this formulation, the pharmaceutically-acceptable organic acid is citric acid, the polyethylene glycol has a molecular weight of about 300, the lower alcohol is ethanol and the surfactant is polysorbate-80.

Yet another embodiment of the invention is an formulation comprising a solution providing a total dose of approximately 0.1 mg/m$^2$ to approximately 100 mg/m$^2$ of the novel deuterated Karenitecin® analog, pharmaceutically-acceptable salt, and/or derivative thereof, dissolved in approximately 1 to approximately 10 parts by weight of N-methylpyrrolidinone, dimethylisosorbide and/or dimethylacetamide in the presence of approximately 0.1 to 0.5 parts by weight of a pharmaceutically-acceptable organic carboxylic acid. This formulation further comprises approximately 5 to approximately 9 parts by weight of polyethylene glycol, approximately 0.1 to approximately 2.0 parts by weight of a pharmaceutically-acceptable alcohol, and approximately 1 to approximately 10 parts by weight of a non-ionic surfactant. More preferred for this aforementioned formulation is when the acid is citric acid, the polyethylene glycol has a molecular weight of about 300, the alcohol is ethanol, and the surfactant is polysorbate-80.

Another embodiment of the present invention is an formulation comprising a solution providing a total dose of approximately 0.1 mg/m$^2$ to approximately 100 mg/m$^2$ of the novel deuterated Karenitecin® analog, pharmaceutically-acceptable salt, and/or derivative thereof, dissolved in approximately 1 to approximately 10 parts by weight of N-methylpyrrolidinone, dimethylisosorbide and/or dimethylacetamide in the presence of approximately 0.1 to approximately 0.5 parts by weight of a pharmaceutically-acceptable organic carboxylic acid. This solution further comprises approximately 0.1 to approximately 2.0 parts by weight of a pharmaceutically-acceptable alcohol, and approximately 1 to approximately 10 parts by weight of a non-ionic surfactant. More specifically, for this formulation, the acid is citric or phosphoric acid, the alcohol is ethanol, and the non-ionic surfactant is comprised of polyoxyethylated castor oil.

Another embodiment of the present invention is an formulation comprising a solution providing a total dose of approximately 0.1 mg/m$^2$ to approximately 100 mg/m$^2$ of the novel deuterated Karenitecin® analog, pharmaceutically-acceptable salt, and/or derivative thereof, dissolved in approximately 1 to approximately 10 parts by weight of N-methylpyrrolidinone, dimethylisosorbide and/or dimethylacetamide, wherein this solution further comprises approximately 1 to approximately 10 parts by weight polyoxyethylated castor oil, approximately 0.1 to approximately 2 parts by weight dehydrated ethyl alcohol USP, and approximately 0.1 to approximately 0.9 parts by weight citric acid.

In a preferred parenteral formulation, the novel deuterated Karenitecin® analog, pharmaceutically-acceptable salt, and/or derivative thereof, is solubilized in a manner suitable for clinical use by forming a sterile, nonaqueous solution of 1 part of said novel deuterated Karenitecin® analog, pharmaceutically-acceptable salt, and/or derivative thereof per 1 to 2 mL of a vehicle comprising dehydrated ethyl alcohol 0.1-2.0 parts by weight, benzyl alcohol 0.1-2.0 parts by weight, citric acid 0.1-0.9 parts by weight, polyethylene glycol (molecular weight 200-300) 4 to 10 parts by weight, polysorbate-80 (Tween 80) 1 to 10 parts, and dimethylisosorbide 1 to 10 parts by weight, contained within an acidified medium with an overall pH of approximately 3 to 4.

Another preferred parenteral formulation comprises the novel deuterated Karenitecin® analog, pharmaceutically-acceptable salt, and/or derivative thereof, formulated for dilution prior to parenteral administration providing a total dose of approximately 0.1 mg/m$^2$ to 100 mg/m$^2$ of said novel deuterated Karenitecin® analog, pharmaceutically-acceptable salt, and/or derivative thereof per 2 mL of nonaqueous solvents including, but not limited to, 1 to 10 parts by weight Cremaphor EL™ (polyoxyethylated castor oil), 0.1 to 2 parts by weight dehydrated ethyl alcohol USP, dimethylisosorbide 1 to 10 parts by weight, and citric acid 0.1-0.9 parts by weight to adjust the final pH to between approximately 3 to 4.

One embodiment of the present invention is a method for administration of said novel deuterated Karenitecin® analog, pharmaceutically-acceptable salt, and/or derivative thereof to a subject with cancer, comprising infusing from about 0.1 mg/m$^2$ to about 100 mg/m$^2$ of the novel deuterated Karenitecin® analog, pharmaceutically-acceptable salt, derivative, prodrug, conjugate, hydrate, solvate, polymorph, and/or tautomeric form thereof, wherein the selected dose is administered at least once over approximately 24 hours and repeated for at least two consecutive days, dependant upon the condition of the subject and the type of cancer or cancers effecting said subject.

Yet another embodiment of the present invention discloses a method for administration of said novel deuterated Karenitecin® analog, pharmaceutically-acceptable salt, and/or derivative thereof to a subject with cancer comprising continuously infusing from about 0.1 mg/m$^2$ to about 100 mg/m$^2$ of said novel deuterated Karenitecin® analog, pharmaceutically-acceptable salt, and/or derivative thereof, over a duration of approximately 24 to 120 hours every 21 to 28 days.

One embodiment discloses a method for the administration of a formulation comprising said novel deuterated Karenitecin® analog, pharmaceutically-acceptable salt, and/or derivative thereof to a subject with cancer, comprising of infusing from approximately 0.1 mg/m$^2$ to approximately 100 mg/m$^2$ of said formulation over a duration of approximately 120 minutes, given once per week for three consecutive weeks with 2 weeks rest after each 3 week cycle, wherein said formulation is sterilized and prepared for oral, intrapleural, intrathecal, intracisternal, intravesicular, intraperitoneal, topical or parenteral administration to a subject with cancer.

One embodiment discloses a method for the administration of a formulation comprising said novel deuterated Karenitecin® analog, pharmaceutically-acceptable salt, and/or derivative thereof to a subject with cancer, said method comprising of infusing from approximately 0.1 mg/m$^2$ to approximately 75 mg/m$^2$ of said formulation over a duration of approximately 120 minutes, given once per week for three consecutive weeks with 2 weeks rest after each 3 week cycle, wherein said formulation is sterilized and prepared for oral, intrapleural, intrathecal, intracisternal, intravesicular, intraperitoneal, topical or parenteral administration to a subject with cancer.

One embodiment discloses a method for the administration of a formulation comprising said novel deuterated Karenitecin® analog, pharmaceutically-acceptable salt, and/or derivative thereof to a subject with cancer, said method comprising of infusing from approximately 0.1 mg/m$^2$ to approximately 50 mg/m$^2$ of said formulation over a duration of approximately 120 minutes, given once per week for three consecutive weeks with 2 weeks rest after each 3 week cycle, wherein said formulation is sterilized and prepared for oral, intrapleural, intrathecal, intracisternal, intravesicular, intraperitoneal, topical or parenteral administration to a subject with cancer.

One embodiment discloses a method for the parenteral administration of a formulation comprising said novel deuterated Karenitecin® analog, pharmaceutically-acceptable salt, and/or derivative thereof to a subject with cancer, said method comprising of infusing from approximately 0.1 mg/m$^2$ to approximately 100 mg/m$^2$ of said formulation over a duration of approximately 120 minutes every 21 to 28 days.

One embodiment discloses a method for the parenteral administration of a formulation comprising said novel deuterated Karenitecin® analog, pharmaceutically-acceptable salt, and/or derivative thereof, to a subject with cancer, said method comprising of infusing from approximately 0.1 mg/m$^2$ to approximately 75 mg/m$^2$ of said formulation over a duration of approximately 120 minutes every 21 to 28 days.

One embodiment discloses a method for the parenteral administration of a formulation comprising said novel deuterated Karenitecin® analog, pharmaceutically-acceptable salt, and/or derivative thereof to a subject with cancer, said method comprising of infusing from approximately 0.1 mg/m$^2$ to approximately 50 mg/m$^2$ of said formulation over a duration of approximately 120 minutes for three consecutive days every 21 to 28 days.

In one embodiment of the present invention the method is carried out to treat cancer in a subject. In another embodiment the subject is a human with cancer, wherein said cancer includes, as non-limiting examples, one or more cancers of the non-small cell lung cancer, adenocarcinoma, renal cell cancer, metastatic soft tissue sarcoma, ovarian cancer, fallopian tube cancer, primary peritoneal cancer, malignant glioma, neuroendocrine carcinoma, nasopharyngeal carcinoma, prostate cancer, and urothelial cancer, melanoma, breast cancer, prostatic carcinoma, kidney carcinoma, bladder carcinoma, pancreatic carcinoma, thyroid carcinoma, lung carcinoma, colon carcinoma, endometrial carcinoma, rectal carcinoma, brain carcinoma, liver carcinoma, and ovarian carcinoma, as well as all known solid forms of cancer (e.g., tumors), lymphomas, and leukemias.

It should be noted that both the site and type of tumor to be treated will, in many cases, influence the preferred route of administration and therapeutic regimen to be applied. Consequently, although the disclosed formulations of the present invention may be most usually administered by intravenous injection or infusion, they also can be delivered directly into the tumor site or by other methods designed to target the drug directly to the tumor site. For example, in subjects with malignant pleural effusion, the intrapleural route may be preferred; in subjects with poor venous access the subcutaneous route of administration may be preferred; in subjects with primary or metastatic cancer involving the brain or nervous system, the intracisternal or intrathecal route of administration may be most advantageous; in subjects with malignant ascites secondary to cancer, one may select intraperitoneal administration; and in subjects with bladder cancer direct intravesicular instillation may be most advantageous. Similarly, in tumors of the skin, the formulation may be topically applied. An oral formulation is also provided for use where suitable.

Thus, an additional embodiment of the present invention is a solution comprising the novel deuterated Karenitecin® analog, pharmaceutically-acceptable salt, and/or derivative thereof, dissolved in N-methylpyrrolidinone, dimethylisosorbide and/or dimethylacetamide, in the presence of a pharmaceutically-acceptable acid and this solution is sterilized and prepared for oral, intrapleural, intrathecal, subcutaneous, intracisternal, intravesicular, intraperitoneal, topical or parenteral administration to a subject with cancer.

The disclosed formulations of the present invention may also be utilized in conjunction with one or more other chemotherapeutic agents in methods of convergent therapy whereupon an additional drug or drugs are co-administered along with the claimed formulation. Thus, the novel deuterated Karenitecin® analog, pharmaceutically-acceptable salt, and/or derivative thereof, may also be administered with one or more other chemotherapeutic agents including, but not limited to: a fluropyrimidine; a pyrimidine nucleoside; a purine nucleoside; an antifolate, a platinum analog; an anthracycline/anthracenedione; an epipodopodophyllotoxin; a camptothecin; a hormone, a hormonal analog; an antihormonal; an enzyme, protein, peptide, or antibody; a vinca alkaloid; a taxane; an epothilone; an antimicrotubule agent; an alkylating agent; an antimetabolite; a topoisomerase inhibitor; an antiviral; or a cytostatic agent.

Fluropyrimidines include, for example, 5-fluorouracil [5-FU], S-1 capecitabine, ftorafur, 5'deoxyflurouridine, UFT, eniluracil, and the like. Pyrimidine nucleosides include, for example, cytarabine, deoxycytidine, 5-azacytosine, gemcitabine, 5-azadeoxycytidine, and the like. Purine nucleosides include, for example, fludarabine, 6-mercaptopurine, thioguanine, allopurinol, cladribine, 2-chloro adenosine. Anti-folates include, for example, methotrexate (MTX), trimetrexate, aminopterin, and methylene-10-deazaaminopterin (MDAM). Platinum analogs include, for example, cisplatin, carboplatin, oxaplatin, picoplatin, tetraplatin, platinum-DACH and analogs thereof.

Anthracyclines/anthracenediones include, for example, doxorubicin, daunorubicin, epirubicin, and idarubicin. Epipodophyllotoxin derivatives include, for example, etoposide, etoposide phosphate and teniposide. Camptothecins include, for example, irinotecan, topotecan, 9-aminocamptothecin, 10,11-methylenedioxycamptothecin, karenitecin, 9-nitrocamtothecin, and TAS 103. Hormones and hormonal analogs may include, for example, estrogens and estrogen analogs, including anastrazole, diethylstilbesterol, estradiol, premarin, raloxifene; progesterone, progesterone analogs and progestins, including progesterone, norethynodrel, esthisterone, dimesthisterone, megestrol acetate, medroxyprogesterone acetate, hydroxyprogesterone caproate, and norethisterone; androgens, including fluoxymesterone, methyltestosterone and testosterone; adrenocorticosteroids, including dexamthasone. Antihormones include, for example, antiestrogens, including, tamoxifen, fulvestrant, toremifene; aminoglutethimide, testolactone, droloxifene, anastrozole; antiandrogens, including, bicalutamide, flutamide, nilutamide, goserelin; antitestosterones, including flutamide, leuprolide, triptorelin; adrenal steroid inhibitors including, aminoglutethimide and mitotane; and anti-leuteinizing, including goserelin. Enzymes, proteins, peptides and antibodies include, for example, asparaginase, cetuximab, erlotinib, bevacizumab, rituximab, gefitinib, trastuzumab, interleukins, interferons, leuprolide, pegasparanase, and the like. Vinca Alkaloids include, for example, vincristine, vinblastine, vinorelbine, vindesine, and like. Taxanes include, for example, paclitaxel, docetaxel, and formulations and analogs thereof. Alkylating agents may include, for example, dacarbazine; procarbazine; temozolamide; thiotepa; nitrogen mustards (e.g., mechlorethamine, chlorambucil, L-phenylalanine mustard, melphelan, and the like); oxazaphosphorines (e.g., ifosphamide, cyclophosphamide, mefosphamide, perfosfamide, trophosphamide and the like); alkyl sulfonates (e.g., busulfan); and nitrosoureas (e.g., carmustine, lomustine, semustine and the like). Epothilones include, for example, epothilones A-E. Antimetabolites include, for example, tomudex and methotrexate, 6-mercaptopurine, 6-thioguanine. Topoisomerase inhibitors include, for example, irinotecan, and topotecan, karenitecin, amsacrine, etoposide, etoposide phosphate, teniposide, and doxorubicin, daunorubicin, and other analogs. Antiviral agents include, for example, acyclovir, valacyclovir, ganciclovir, amantadine, rimantadine, lamivudine, and zidovudine. Cytostatic agents include, for example, bevacizumab, trastuzumab, rituximab, and the like, as well as growth inhibitors such as erlotinib, and the like. In general, cytostatic agents are mechanism-based agents that slow the progression of neoplastic disease.

When the novel deuterated Karenitecin® analog, pharmaceutically-acceptable salt, and/or derivative thereof, dissolved in N-methylpyrrolidinone, dimethylisosorbide and/or dimethylacetamide is administered parenterally, the formulation is preferably diluted with an appropriate volume of a parenteral vehicle to a concentration so a to provide a total dose of approximately 0.1 mg/m$^2$ to approximately 100 mg/m$^2$ of the novel deuterated Karenitecin® analog, pharmaceutically-acceptable salt, and/or derivative thereof. A further embodiment of the claimed invention is a sterile solution of any of the claimed novel deuterated Karenitecin® analog formulations for sterile administration to a subject with cancer upon dilution with a sterile parenteral vehicle. For the purposes of the present invention, parenteral vehicles include dextrose approximately 5% to approximately 10% in water, approximately 0.9% NaCl in water (with or without 5% or 10% Dextrose), approximately 0.45% NaCl in water (with or without 5% or 10% Dextrose), and approximately 3% NaCl in water (with or without 5% to 10% Dextrose), or sterile lipid formulations, such as intralipid, used for parenteral nutritional support for cancer subjects.

Clinicians will administer said novel deuterated Karenitecin® analog, pharmaceutically-acceptable salt, and/or derivative thereof to subjects with cancer, including human subjects, according to schedules that maximize its potential chemotherapeutic effects and diminish its potential toxic side effects. Except at extremely high doses which produce high plasma concentrations of the drugs, the chemotherapeutic activity of said novel deuterated Karenitecin® analog, pharmaceutically-acceptable salt, and/or derivative thereof, can be increased by increasing the duration of exposure (i.e., time dependent) rather than increasing the dose (i.e., dose dependent) of the drug. The greater chemotherapeutic effects associated with increasing the duration of exposure is a finding that is most likely related to the predominant S-phase mode of chemotherapeutic activity of said novel deuterated Karenitecin® analog, pharmaceutically-acceptable salt, and/or derivative thereof The novel deuterated Karenitecin® analog, pharmaceutically-acceptable salt, and/or derivative thereof, is an S-phase-active agent; therefore, the greatest chemotherapeutic effect in, e.g., human subjects, will likely be observed with prolonged infusion or closely spaced repetitive administration schedules. Such schedules of administration would expose more cycling tumor cells to the drug and increase the frequency of exposure of the tumor cells in S-phase to sufficiently toxic levels of the drug.

B. Oral and Rectal Formulations and Administration

Oral formulations include tablets, suspensions, solutions, gelatin capsules (hard or soft), dissolvable tablets, troche, and the like. It should be noted that with sublingual administration, first-pass metabolism through the liver (i.e., the cytochrome $P_{450}$ oxidase system) is avoided The above-mentioned compositions and formulations include as their active ingredient said novel deuterated Karenitecin® analog, pharmaceutically-acceptable salt, and/or derivative thereof, as set forth herein. Highly Lipophilic Camptothecin Analogs (HLCDs), as that term is recognized within the art, are defined as having a water solubility of less than 5 µg/mL of water.

When oral dosages are to be administered in a capsule form, it is clearly superior to have a concentrated solution of the novel deuterated Karenitecin® analog, pharmaceutically-acceptable salt, derivative, prodrug, conjugate, hydrate, solvate, polymorph, and/or tautomeric form thereof, suitable for encapsulation within a soft or hard gelatin capsule. Concentrated solutions allow the preparation of capsules of smaller size which allows easier ingestion by the subject, and may also reduce the number of capsules to be swallowed. These factors are important in view of the generally poor condition of cancer subjects.

Taurocholic acid, a bile acid, may enhance in the intestinal absorption of the drug in certain subjects. The present invention takes advantage of the discovery that taurocholic acid, or a pharmaceutically-acceptable salt thereof, when included with the novel deuterated Karenitecin® analog, pharmaceutically-acceptable salt, and/or derivative thereof, in a solution dosage formulation, results in improved absorption of the drug following ingestion of the formulation. It is believed that this is due to the formation of a micellar solution of the novel deuterated Karenitecin® analog, pharmaceutically-acceptable salt, and/or derivative thereof, on dilution thereof with the gastric contents.

The phenomenon of micellar solubilization of poorly water-soluble drugs mediated by bile acids, including taurocholic acid, has been previously reported with respect to glutethimide, hexesterol, griseofulvin (see, e.g., Bates, et al., Rates of Dissolution of Griseofulvin and Hexestrol in Bile Salt Solutions. Chem. Abstracts 65:8680b (1966); Bates, et al., Solubilizing Properties of Bile Salt Solutions on Glutethimide, Griseofulvin, and Hexestrol. Chem. Abstracts 64:9517e (1966); reserpine (see, e.g., Malone, et al., Desoxycholic Acid Enhancement of Orally Administered Reserpine. J. Pharmaceutical Sci. 55:972-974 (1966) and fatty acids and cholesterol (see, e.g., Westergaard, et al., The Mechanism Whereby Bile Acid Mycelles Increase the Rate of Fatty Acid and Cholesterol Uptake Into the Intestinal Mucosal Cell. J. Clinical Invest. 58:97-108 (1976). The use of taurocholic acid or a pharmaceutically-acceptable salt thereof in the present invention involves a pharmaceutical solution of the novel deuterated Karenitecin® analog, pharmaceutically-acceptable salt, and/or derivative thereof, which has the unique property of providing a stable apparent solution of the drug upon dilution thereof with from 1 to 100 volumes of water. The solution is stable and free of precipitate for a period of at least two hours; sufficient time to permit administration and absorption by the subject.

It has been observed with similar solutions of etoposide, a different insoluble anti-cancer drug, that the bioavailability of the drug following oral administration is substantially equivalent to that achieved by intravenous administration of a solution of etoposide (U.S. Pat. No. 4,713,246). Analogous to that found with etoposide, it is believed that ingestion of the present dosage form of the novel deuterated Karenitecin® analog, pharmaceutically-acceptable salt, and/or derivative thereof, and resulting dilution thereof by the stomach contents, results in the formation of a micellar solution of the novel deuterated Karenitecin® analog in the stomach which is readily absorbed by the gastrointestinal tract. It should be noted, however, that Applicants do not wish to be bound by any theoretical explanation of the mechanism by which the superior oral bioavailability of the present novel deuterated Karenitecin® analog formulations is achieved.

Other embodiments of the present invention for oral administration to a subject with cancer said of novel deuterated Karenitecin® analog, pharmaceutically-acceptable salt, and/or derivative thereof, dissolved in N-methylpyrrolidinone (NMP) in the presence of a pharmaceutically-acceptable acid; said novel deuterated Karenitecin® analog, pharmaceutically-acceptable salt, and/or derivative thereof, dissolved in dimethylisosorbide (DMI) in the presence of a pharmaceutically-acceptable acid; or said novel deuterated Karenitecin® analog, pharmaceutically-acceptable salt, and/or derivative thereof, is dissolved in dimethylacetamide (DMA) in the presence of a pharmaceutically-acceptable acid.

A further embodiment of the present invention is the claimed formulation and method of administering the formulation by encapsulating the claimed formulations within a hard gelatin capsule. Still yet another embodiment of the claimed formulation and method of administering the formulation is encapsulating the claimed formulations within a soft gelatin capsule. One of ordinary skill in the art will know that any of the claimed formulations adapted for oral administration can be used as the fill for the soft or hard gelatin capsule.

Another embodiment of the present invention is an oral formulation of said novel deuterated Karenitecin® analog, pharmaceutically-acceptable salt, and/or derivative thereof, in soft gelatin capsules (comprised of, for example, gelatin/glycerin/sorbitol/purifiers) containing 1.0 part of said novel deuterated Karenitecin® analog, pharmaceutically-acceptable salt, and/or derivative thereof, in a vehicle comprising citric acid 0.1 to 0.9 parts by weight, glycerin 1 to 10 parts by weight, polyethylene glycol (molecular weight 200 to 300) 5 to 9 parts by weight, dehydrated ethyl alcohol 10 to 20% by weight of total solution weight, sodium acetate 0.05 to 0.5 parts by weight, a surfactant, and 1 to 10 parts dimethylisosorbide by weight. A more preferred oral formulation will include as a surfactant, pluronic F-127 poloxamer at 0.05 to 1.0 parts by weight.

Another preferred oral formulation will include the addition of taurocholic acid 2 to 10 parts by weight. The soft gelatine capsules may also be composed of any of a number of compounds used for this purpose including, but not limited to, a mixture of gelatine, glycerin, sorbitol, and parabens.

The present invention also provides for the formulation of the novel deuterated Karenitecin® analog, pharmaceutically-acceptable salt, and/or derivative thereof, for rectal delivery and absorption via the utilization of rectal suppositories or retention enemas. Generally, suppositories are utilized for delivery of drugs to the rectum and sigmoid colon. The ideal suppository base for the delivery of the formulations of the present invention should meet the following specifications: (i) a base which is non-toxic and non-irritating to the anal mucous membranes; (ii) a base which is compatible with a variety of drugs; (iii) a bases with melts or dissolves in rectal fluids; and (iv) a base which is stable in storage and does not bind or otherwise interfere with the release and/or absorption of the pharmaceutical formulations contained therein. Typical suppository bases include: cocoa butter, glycerinated gelatine, hydrogenated vegetable oils, mixtures of polyethylene glycols of various molecular weights and fatty acid esters of polyethylene glycol. The rectal epithelium is lipoidal in character. The lower, middle, and upper hemorrhoidal veins surrounds the rectum. Only the upper vein conveys blood into the portal system, thus drugs absorbed into the lower and middle hemorrhoidal veins will bypass the liver and the cytochrome $P_{450}$ oxidase system. Absorption and distribution of a drug is therefore modified by its position within the rectum, in that at least a portion of the drug absorbed from the rectum may pass directly into the inferior vena cava, bypassing the liver. The present invention also provides for the formulation of said novel deuterated Karenitecin® analog, pharmaceutically-acceptable salt, and/or derivative thereof, as well as one or more chemotherapeutic agents, administered by suppository.

One embodiment discloses a method for the oral administration of a formulation comprising said novel deuterated Karenitecin® analog, pharmaceutically-acceptable salt, and/or derivative thereof, to a subject with cancer, said method consisting of administering from approximately 0.1 mg/m² to approximately 100 mg/m² of said formulation in single or divided dosages within a 24 hour period every 21 to 28 days.

One embodiment discloses a method for the oral administration of a formulation comprising said novel deuterated Karenitecin® analog, pharmaceutically-acceptable salt, and/or derivative thereof, to a subject with cancer, said method consisting of administering from approximately 0.1 mg/m² to approximately 75 mg/m² of said formulation daily in single or divided doses for three consecutive days every 21 to 28 days.

One embodiment discloses a method for the oral administration of a formulation comprising said novel deuterated Karenitecin® analog, pharmaceutically-acceptable salt, and/or derivative thereof, to a subject with cancer, said method consisting of administering from approximately 0.1 mg/m² to approximately 50 mg/m² of said formulation daily in single or divided doses for three consecutive days every 21 to 28 days.

Another embodiment discloses a method for the oral administration of a formulation comprising said novel deuterated Karenitecin® analog, pharmaceutically-acceptable salt, and/or derivative thereof, to a subject with cancer, said method consisting of administering from approximately 0.1 mg/m² to approximately 100 mg/m² of said formulation in single or divided dosages within a 24 hour period given once per week for three consecutive weeks with 2 weeks rest after each 3 week cycle.

One embodiment discloses a method for the oral administration of a formulation comprising said novel deuterated Karenitecin® analog, pharmaceutically-acceptable salt, and/or derivative thereof, to a subject with cancer, said method consisting of administering from approximately 0.1 mg/m² to approximately 75 mg/m² of said formulation in single or divided doses within a 24 hour period once per week for three consecutive weeks with 2 weeks rest after each 3 week cycle.

Another embodiment discloses a method for the oral administration of a formulation comprising said novel deuterated Karenitecin® analog, pharmaceutically-acceptable salt, and/or derivative thereof, to a subject with cancer, said method consisting of administering from approximately 0.1 mg/m² to approximately 50 mg/m² of said formulation in single or divided dosages within a 24 hour period given once per week for three consecutive weeks with 2 weeks rest after each 3 week cycle.

One embodiment discloses a method for the oral administration of a formulation comprising said novel deuterated Karenitecin® analog, pharmaceutically-acceptable salt, and/or derivative thereof, to a subject with cancer, said method consisting of administering from approximately 0.1 mg/m²/day to approximately 100 mg/m²/day of said formulation in single or divided daily doses administered within each 24 hour period for two to five consecutive days and repeated every 21 to 28 days.

One embodiment discloses a method for the oral administration of a formulation comprising said novel deuterated Karenitecin® analog, pharmaceutically-acceptable salt, and/or derivative thereof, to a subject with cancer, said method consisting of administering from approximately 0.1 mg/m²/day to approximately 75 mg/m²/day of said formulation in single or divided daily doses administered within each 24 hour period for two to five consecutive days and repeated every 21 to 28 days.

One embodiment discloses a method for the oral administration of a formulation comprising said novel deuterated Karenitecin® analog, pharmaceutically-acceptable salt, and/or derivative thereof, to a subject with cancer, said method consisting of administering from approximately 0.1 mg/m²/day to approximately 50 mg/m²/day of said formulation in single or divided daily doses administered within each 24 hour period for two to five consecutive days and repeated every 21 to 28 days.

SPECIFIC EXAMPLES OF FORMULATIONS OF THE PRESENT INVENTION

In its preferred embodiments, the present invention involves the preparation and administration of novel deuterated Karenitecin® analog formulations. The following examples of the administration of these formulations illustrate selected modes for carrying out the present invention, and are not to be construed as limiting in any way.

Example I

For injection or infusion into aqueous body fluids, a formulation comprises a total dose of from approximately 0.1 mg/m² to approximately 100 mg/m² of the novel deuterated Karenitecin® analog, pharmaceutically-acceptable salt, and/or derivative thereof, dissolved in 1 to 10 parts of N-methylpyrrolidinone, dimethylisosorbide and/or dimethylacetamide in an acidified vehicle comprising between approximately 10 to approximately 40 percent of an acceptable alcohol, approximately 4 to approximately 10 parts by weight of polyether glycol, and approximately 1 to approximately 10 parts of a non-ionic surfactant. Suitable alcohols include dehydrated ethyl alcohol, benzyl alcohol. Suitable polyether glycols, include polyethylene glycol 200, polyethylene glycol 300, propylene glycol. Suitable non-ionic surfactants include, but are not limited to, polysorbate-80. In a preferred embodiment, the formulation of the novel deuterated Karenitecin® analog, pharmaceutically-acceptable salt, and/or derivative thereof, is supplied as an intravenous injectable in a 1 mg vial comprising a sterile, nonaqueous solution of drug in a vehicle comprising dehydrated ethyl alcohol, benzyl alcohol, citric acid, polyethylene glycol 300, and polysorbate (Tween 80) in acidified medium with a pH of 3 to 4 at a final concentration of 1 mg per 1 to 2 mL of total volume.

Example II

A second formulation comprises a total dose of from approximately 0.1 mg/m² to approximately 100 mg/m² of the novel deuterated Karenitecin® analog, pharmaceutically-acceptable salt, and/or derivative thereof, in an acidified vehicle comprising between approximately 0.1 to 2 parts of an alcohol and approximately 1 to 10 parts of a non-ionic surfactant. Suitable alcohols include dehydrated ethyl alcohol USP, and benzyl alcohol. Suitable non-ionic surfactants include the polyoxyethylated oils, such as polyoxyethylated vegetable oils, such as castor oil, peanut oil, and olive oil. In a preferred embodiment 1 mg to 200 mg the novel deuterated Karenitecin® analog, pharmaceutically-acceptable salt, derivative, pharmaceutically-acceptable salt, and/or derivative thereof, is formulated in 1 to 10 parts of N-methylpyrrolidinone, dimethylisosorbide and/or dimethylacetamide, 1 to 10 parts of Cremaphor EL™ (polyoxyethylated castor oil), 0.1 to 2 parts by weight dehydrated ethyl alcohol USP, and 0.1 to 0.9 parts citric acid to adjust the final pH between 3 to 4.

Example III

An oral formulation of the novel deuterated Karenitecin® analog in soft gelatin capsules (e.g., comprised of gelatin/glycerin/sorbitol/purifiers) containing 1.0 part of the novel deuterated Karenitecin® analog, pharmaceutically-acceptable salt, and/or derivative thereof, in 1 to 10 parts of N-methylpyrrolidinone, dimethylisosorbide and/or dimethylacetamide, citric acid 0.1 to 0.5 parts by weight, glycerin 1 to 10 parts by weight, and polyethylene glycol 200 to 300-5 to 9 parts by weight, dehydrated ethyl alcohol 0.2 to 2 parts by weight of total solution weight, sodium acetate 0.05 to 0.5 parts by weight, pluronic poloxamer using 0.05 to 1.0 parts by weight, and taurocholic acid 2 to 10 parts by weight. The soft gelatin capsules may also be composed of any of a number of compounds used for this purpose including, for example, a mixture of gelatin, glycerin, sorbitol, and parabens.

It should be noted that in order to prolong the stability and solubility of the novel deuterated Karenitecin® analog for clinical infusions, the drug may diluted in 5% Dextrose in water (D5W) to a final concentration so as to provide a total dose of approximately 0.1 mg/m² to approximately 100 mg/m² of the novel deuterated Karenitecin® analog, pharmaceutically-acceptable salt, and/or derivative thereof, prior to injection or infusion.

Maintaining an acidic pH (i.e., pH 3 to 4) in the formulation is particularly important to reduce the slow conversion of the lactone-conformation of the deuterated Karenitecin® analog (i.e., active form) to the E-ring-hydrolyzed carboxylate (i.e., inactive form), which occurs at physiological pH. At equilibrium under physiologic pH, the ratio of the inactive, "open-ring" carboxylate form to "closed-ring" lactone form, increases. Hence, hydrolysis of the lactone ring will be substantially reduced if the drug is kept in an acidic environment. The lactone E-ring form of, e.g., naturally-occurring camptothecin, as in the deuterated Karenitecin® analog of the present invention, is less water soluble than the carboxylate E-ring form. As previously discussed, when early clinical trials were first conducted with camptothecin using NaOH, the significance of maintaining the closed lactone ring for uniform efficacy in treating subjects with cancer was poorly understood. The early reported unpredictable clinical toxicities associated with camptothecin administration may have been exacerbated by the NaOH formulation which promotes the formation of the carboxylate form, and by the relative lack of understanding of the significance of the lactone form of camptothecin as it relates to chemotherapeutic activity.

SPECIFIC EXAMPLES OF THE ADMINISTRATION OF FORMULATIONS

The foregoing description of the formulation invention has been directed to particular preferred embodiments in accordance with the requirements of the patent statutes and for purposes of explanation and illustration. Those skilled in the art will recognize that many modifications and changes may be made without departing from the scope and the spirit of the invention.

The administration of the novel deuterated Karenitecin® analogs, pharmaceutically-acceptable salts, and/or derivative thereof, of the present invention may be carried out using various schedules and dosages.

These specific examples include, but are not limited to:

(1) For intravenous administration, a suitable dose is approximately 0.1 mg/m² to approximately 100 mg/m² in a 24 hour period which can be administered in a single or divided into multiple doses, depending upon the attending physician. This dosing regimen may be repeated for 48 hours or more. Other suitable intravenous dosing schedules range from approximately 0.1 mg/m² to approximately 100 mg/m² per day using a 3 to 5 day continuous infusion schedule every 21 to 30 days and approximately 0.1 mg/m² to approximately 100 mg/m² given as a 30 to 90 minute infusion every 21 to 30 days.

(2) A suitable oral dose of the drug is approximately 0.1 mg/m² to approximately 100 mg/m² per day using the lower dose for a period of 3 to 5 days and using divided dosages of administration of two to four times per day. Other suitable oral dosing schedules range from approximately 0.1 mg/m² to approximately 75 mg/m² per day for a period of 3 to 5 days and approximately 0.1 mg/m² to approximately 50 mg/m² per day for a period of 3 to 5 days.

It should be noted that the parenteral and oral doses can be administered under the supervision of a physician based on gradual escalation of the dosage to achieve the maximum tolerated dose in the individual subject. The oral administration schedule of the novel deuterated Karenitecin® analogs, pharmaceutically-acceptable salts, and/or derivatives thereof, may involve multiple daily doses or single daily doses for one or more consecutive days with the ability of the physician to optimize therapy by reaching the maximum effective chemotherapeutic dose that has the least toxicity in the individual subject.

In addition, subjects may be given the novel deuterated Karenitecin® analogs, pharmaceutically-acceptable salts, and/or derivatives thereof, of the present invention as either an inpatient or outpatient, using the following exemplary schedules:

(1) approximately 0.1 mg/m² to approximately 100 mg/m² given over 90 minutes I.V. every 21 to 28 days;
(2) approximately 0.1 mg/m² to approximately 100 mg/m² given daily for three consecutive days over 90 minutes I.V. every 21 to 28 days;
(3) approximately 0.1 mg/m² to approximately 100 mg/m² week given once per week×3 consecutive weeks over 90 minutes i.v. with 2 weeks rest after each 3 week cycle for pretreated subjects;
(4) approximately 0.1 mg/m² to approximately 100 mg/m² given once per week×3 consecutive weeks over 90 minutes I.V. for previously untreated subjects with 2 weeks rest after each 3 week cycle; and
(5) approximately 0.1 mg/m²/day to approximately 100 mg/m²/day×3-5 consecutive days as a continuous i.v. infusion every 21 to 28 days.

In a preferred embodiment, the novel deuterated Karenitecin® analog, pharmaceutically-acceptable salt, derivative, prodrug, conjugate, hydrate, solvate, polymorph, and/or tautomeric form thereof, is initially given at a lower dose. The dose of the aforementioned novel deuterated Karenitecin® analog is then escalated at each successive cycle of treatment until the subject develops side effects which demonstrates individual therapeutic tolerance. The purpose of dose escalation is to safely increases the drug levels to a maximum tolerated dose and should result in increased cytotoxicity and improved chemotherapeutic activity.

Dosages can be escalated based on subject tolerance as long as unacceptable toxicity is not observed. "Unacceptable toxicity" is defined by World Health Organization (WHO) as grade 3 non-hematologic toxicity excluding nausea and vomiting and grade 4 vomiting or hematologic toxicity according to the National Cancer Institute common toxicity criteria. Since some clinical drug toxicity is anticipated in routine clinical oncology practice, appropriate treatment will be used to prevent toxicity (e.g., nausea and vomiting) or ameliorate signs and symptoms if they are observed (e.g., diarrhea). For example, antiemetics will be administered for nausea and vomiting, antidiarrheals for diarrhea, and antipyretics for fever. Appropriate dosages of steroids/antihistamines will also be used to prevent or ameliorate any anaphylactoid toxicity if an anaphylactoid reaction is observed.

Determination of Serum Levels

Kaneda's HPLC method and its further modifications by Barilero, et al., (Simultaneous Determination of the Camptothecin Analogue CPT-11 and Its Active Metabolite HECPT by High Performance Liquid Chromatography: Application to Plasma Pharmacokinetic Studies in Cancer Patients. *J. Chromat.* 575:275-280 (1992)) are useful for the measuring quantities of various camptothecins (including the novel deuterated Karenitecin® analogs of the present invention) in plasma and tissue.

Cytotoxicity Results: Comparison of BNP1350 and its Deuterated Analogs

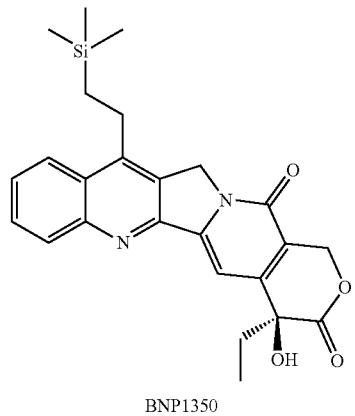

BNP1350

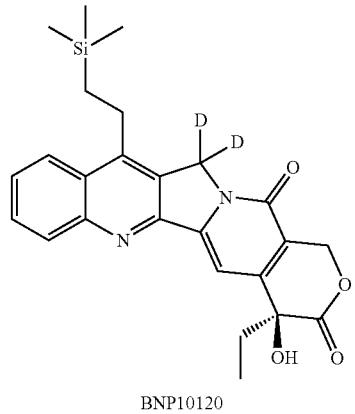

BNP10120

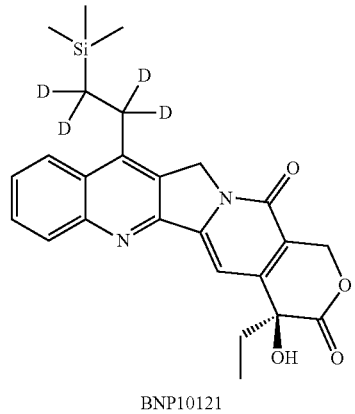

BNP10121

The sulforhodamine B (SRB) assay was used to assess cytotoxicity and absorbance at 570 nm ($A_{570}$) in order to calculate the percentage of cell control (or percent cell survival) for wild-type human ovarian cancer cells (A2780/WT) and doxorubicin-resistant human ovarian cancer cells (A2780/DX5) treated with BNP1350, BNP10120 (a di-deuterated analog of BNP1350) and BNP10121 (a tetra-deuterated analog of BNP1350).

Reagents

Roswell Park Memorial Institute (RPMI 1640) medium, fetal bovine serum (FBS), and L-glutamine were purchased from Gibco BRL. Drugs were dissolved in sterile dimethylsulfoxide (DMSO), from American Type Culture Collection (ATCC) for stock solutions (2.5 to 5.0 mM). Subsequent dilutions were made using cell culture medium (prior to adding the drug to cells). SRB was purchased from Sigma and dissolved in 1.0 percent acetic acid. Trichloroacetic acid was purchased from VWR International. BNP1350, BNP10120 (a di-deuterated analog of BNP1350) and BNP10121 (a tetra-deuterated analog of BNP1350) were synthesized and purified by BioNumerik Pharmaceuticals, Inc.

Instrumentation

Cells were manipulated in a Class IIA/B3 Biological Safety Cabinet (Forma Scientific) and maintained at 37° C. in a humidified atmosphere containing 5% $CO_2$ in a water-jacketed cell culture incubator (Forma Scientific). Cells were counted using a Coulter-Z1 counter (Beckman-Coulter). Following drug treatment, plates were washed using a Biomek 2000 station (Beckman) and, following exposure to SRB dye, plates were washed using an automated plate washer (Model EL404, Bio-Tek Instruments). Percentage of control was correlated to $A_{570}$ values and determined using a Model EL800 plate reader (Bio-Tek Instruments).

Cell Growth and Viability

Wild-type human ovarian cancer cells (A2780/WT) and doxorubicin-resistant human ovarian cancer cells (A2780/DX5) were cultured in RPMI 1640 medium supplemented with 10% fetal bovine serum and 2 mM L-glutamine, and grown in a 37° C. incubator with 5% $CO_2$. Population doubling times for the two cell lines used in this study encompassed a total of five cell doublings corresponding to approximately 5 days for A2780/WT and A2780/DX5 cells. Both cell lines were maintained as monolayered cultures in T-25 or T-75 flasks and then seeded to microtiter plate wells for experiments described herein.

In brief, cells were seeded (500 cells/well in 100 µL total volume) into 96-well microtiter plates and allowed to attach for 24 hours prior to treatment with BNP1350, BNP10120 or BNP10121 for 2 hours. The aforementioned compounds were dissolved in DMSO for use in cytotoxicity experiments where inhibition of cell growth was measured using the SRB assay.

Following this 2 hour drug treatment, the BNP1350, BNP10120 and BNP10121 were removed, cells were washed with drug-free media (200 µL) and then drug-free media (200 µL) was added to the cells and cells were allowed to continue growing at 37° C. with 5% $CO_2$ before the SRB assay was performed (total experiment time from time of seeding was 5 days, during which time a total of 5 cell doublings had occurred).

Prior to SRB assays, cell viability was monitored by evaluation of microtiter plate wells. Dead cells detach and float while living cells remain attached to the bottom of the cell well.

Cytotoxicity Assay (SRB Assay)

The sulforhodamine B (SRB) cytotoxicity assay (see, Skehan P, et al., New colorimetric cytotoxicity assay for anticancer-drug screening. *J. Natl. Cancer Inst.* 82:1107-1112 (1990)) was used to determine the cytotoxic effects of BNP1350, BNP10120 or BNP10121 on cell growth in vitro. Briefly, after the medium was aspirated from individual plate wells, trichloroacetic acid (100 µL of 10.0% solution) was added to each well, and the plates were incubated at 4° C. for at least 1 hour. The plates were washed five-times with water using an automated microplate washer (Model EL 404, Bio-Tek Instruments), SRB solution (100 µL of 0.4 grams SRB dissolved in 100 mL 1.0 percent acetic acid) was added, and plates remained at room temperature for 15 minutes. The plates were then washed five-times using acetic acid (1.0%), air dried, and bound dye was solubilized in Tris base (150 µL, 10 mM). Plates were agitated (gently) for 5 minutes and the absorbance values of the SRB dye-protein adduct at a 570 nm wavelength ($A_{570}$) were determined using an automated microtiter plate reader equipped with an $A_{570}$ filter (Model EL800, BioTek Instruments).

Experimental Results

BNP1350, BNP10120, and BNP10121 were all found to be potent inhibitors of both wild-type (A2780/WT) and doxorubicin resistant (A2780/DX5) ovarian cancer cell growth with nanomolar IC50 values and all of the test articles exhibited potency as shown in Table 1 and FIG. 1.

TABLE 1

Summary of IC50 Determinations in Human Ovarian Cancer Cells

| | IC50 (nM) 2 hour drug treatments | | | |
|---|---|---|---|---|
| | Test 1 | Test 2 | Average | STD |
| A2780/WT | | | | |
| BNP1350 | 1.9 | 1.8 | 1.9 | 0.1 |
| BNP10120 (di-deuterated at C5) | 3.5 | 1.6 | 2.6 | 1.3 |
| BNP10121 (tetra-deuterated at C22, C23) | 6.1 | 6.0 | 6.1 | 0.1 |
| A2780/DX5 | | | | |
| BNP1350 | 7.7 | 6.9 | 7.3 | 0.6 |
| BNP10120 (di-deuterated at C5) | 9.9 | 7.1 | 8.5 | 2.0 |
| BNP10121 (tetra-deuterated at C22, C23) | 12.0 | 11.3 | 11.7 | 0.5 |

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents.

The written description portion of this patent includes all claims. Furthermore, all claims, including all original claims as well as all claims from any and all priority documents, are hereby incorporated by reference in their entirety into the written description portion of the specification, and Applicants reserve the right to physically incorporate into the written description or any other portion of the application, any and all such claims. Thus, for example, under no circumstances may the patent be interpreted as allegedly not providing a written description for a claim on the assertion that the precise wording of the claim is not set forth in haec verba in written description portion of the patent.

The claims will be interpreted according to law. However, and notwithstanding the alleged or perceived ease or difficulty of interpreting any claim or portion thereof, under no circumstances may any adjustment or amendment of a claim or any portion thereof during prosecution of the application or applications leading to this patent be interpreted as having forfeited any right to any and all equivalents thereof that do not form a part of the prior art.

All of the features disclosed in this specification may be combined in any combination. Thus, unless expressly stated otherwise, each feature disclosed is only an example of a generic series of equivalent or similar features.

It is to be understood that while the invention has been described in conjunction with the detailed description thereof, the foregoing description is intended to illustrate and not limit the scope of the invention, which is defined by the scope of the appended claims. Thus, from the foregoing, it will be appreciated that, although specific embodiments of the invention have been described herein for the purpose of illustration, various modifications may be made without deviating from the spirit and scope of the invention. Other aspects, advantages, and modifications are within the scope of the following claims and the present invention is not limited except as by the appended claims.

The specific methods and formulations described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, the terms "comprising", "including", "containing", etc. are to be read expansively and without limitation. The methods and processes illustratively described herein suitably may be practiced in differing orders of steps, and that they are not necessarily restricted to the orders of steps indicated herein or in the claims.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by various embodiments and/or preferred embodiments and optional features, any and all modifications and variations of the concepts herein disclosed that may be resorted to by those skilled in the art are considered to be within the scope of this invention as defined by the appended claims.

The present invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

It is also to be understood that as used herein and in the appended claims, the singular forms "a," "an," and "the" include plural reference unless the context clearly dictates otherwise, the term "X and/or Y" means "X" or "Y" or both "X" and "Y", and the letter "s" following a noun designates both the plural and singular forms of that noun. In addition, where features or aspects of the invention are described in terms of Markush groups, it is intended, and those skilled in the art will recognize, that the invention embraces and is also thereby described in terms of any individual member and any subgroup of members of the Markush group, and applicants reserve the right to revise the application or claims to refer specifically to any individual member or any subgroup of members of the Markush group.

Other embodiments are within the following claims. The patent may not be interpreted to be limited to the specific examples or embodiments or methods specifically and/or expressly disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

What is claimed is:

1. A deuterated analog of (4S)-4-Ethyl-4-hydroxy-11-[2-(trimethylsilyl)ethyl]-1H-pyrano[3',4':6,7]indolizino[1,2-b]quinoline-3,14(4H,12H)-dione (also known as 7-[2-trimethylsilyl)ethyl]-20(S)-camptothecin; BNP1350; and Karenitecin), BNP10120 (4S)-12,12-Dideutero-4-ethyl-4-hydroxy-11-[2-(trimethylsilyl)ethyl]-1H-pyrano[3',4':6,7]indolizino[1,2-b]quinoline-3,14(4H,12H)-dione; wherein BNP10120 consists of the chemical structure illustrated below:

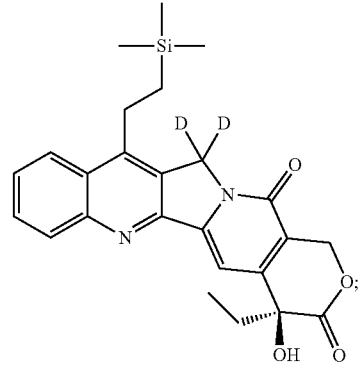 [SMILES: [2H]C1([2H])c2c(nc3ccccc3c2CC[Si](C)(C)C)-c2cc3c(c(=O)n21)COC(=O)[C@]3(O)CC]

and pharmaceutically-acceptable salts thereof.

2. A deuterated analog of (4S)-4-Ethyl-4-hydroxy-11-[2-(trimethylsilyl)ethyl]-1H-pyrano[3',4':6,7]indolizino[1,2-b]quinoline-3,14(4H,12H)-dione (also known as 7-[2-trimethylsilyl)ethyl]-20(S)-camptothecin; BNP1350; and Karenitecin), BNP10121 (S)-4-Ethyl-4-hydroxy-11-[1,1,2,2-tetradeutero-2-(trimethylsilyl)ethyl]-1H-pyrano[3',4':6,7]indolizino[1,2-b]quinoline-3,14(4H,12H)-dione; wherein BNP10121 consists of the chemical structure illustrated below:

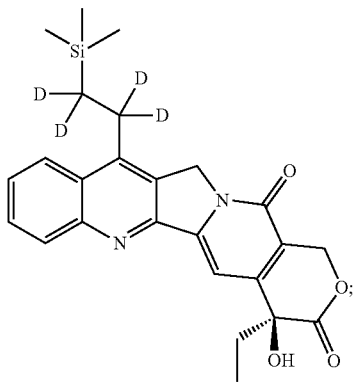 [SMILES: [2H]C([2H])(c1c2c(nc3ccccc13)-c1cc3c(c(=O)n1C2)COC(=O)[C@]3(O)CC)C([2H])([2H])[Si](C)(C)C]

and pharmaceutically-acceptable salts thereof.

3. A deuterated Karenitecin analog of claim 1 or 2, wherein each of the positions represented in the chemical structures as "D" in said analogs have deuterium enrichment of at least 98%.

4. A deuterated Karenitecin analog of claim 1 or 2, wherein each of the positions represented in the chemical structures as "D" in said analogs have deuterium enrichment of at least 90%.

5. A deuterated Karenitecin analog of claim 1 or 2, wherein each of the positions represented in the chemical structures as "D" in said analogs have deuterium enrichment of at least 50%.

6. A deuterated Karenitecin analog of claim 1 or 2, wherein each of the positions represented in the chemical structures as "D" in said analogs have deuterium enrichment of at least 20%.

7. A deuterated Karenitecin analog of claim 1 or 2, wherein each of the positions represented in the chemical structures as "D" in said analogs have deuterium enrichment of at least 10%.

8. A deuterated Karenitecin analog of claim 1 or 2, wherein each of the positions represented in the chemical structures as "D" in said analogs have deuterium enrichment of at least 5%.

9. A deuterated Karenitecin analog of claim 1 or 2, wherein each of the positions in the chemical structures represented as "D" in said analogs have deuterium enrichment of at least 1%.

10. A formulation containing a deuterated Karenitecin analog of claim 1 or 2, to provide a total dose from approximately 0.1 mg/m$^2$ to approximately 100 mg/m$^2$ of said deuterated Karenitecin analog, for administration to a subject with ovarian cancer in need thereof.

11. A formulation containing a deuterated Karenitecin analog of claim 1 or 2, which is administered to a subject in with ovarian cancer need thereof with one or more chemotherapeutic agents.

12. A formulation containing a deuterated Karenitecin analog of claim 1 or 2, wherein said formulation is administered to a subject with ovarian cancer.

\* \* \* \* \*